US012377070B2

(12) United States Patent
Sharma et al.

(10) Patent No.: US 12,377,070 B2
(45) Date of Patent: Aug. 5, 2025

(54) SUBSTITUTED SULFOXIMINE DERIVATIVES

(71) Applicant: CADILA HEALTHCARE LIMITED, Gujarat (IN)

(72) Inventors: Rajiv Sharma, Ahmedabad (IN); Sameer Agarwal, Ahmedabad (IN)

(73) Assignee: Zydus Lifesciences Limited, Gujarat (IN)

( * ) Notice: Subject to any disclaimer, the term of this patent is extended or adjusted under 35 U.S.C. 154(b) by 765 days.

(21) Appl. No.: 17/642,184

(22) PCT Filed: Sep. 11, 2020

(86) PCT No.: PCT/IB2020/058464
§ 371 (c)(1),
(2) Date: Mar. 10, 2022

(87) PCT Pub. No.: WO2021/048809
PCT Pub. Date: Mar. 18, 2021

(65) Prior Publication Data
US 2022/0313657 A1     Oct. 6, 2022

(30) Foreign Application Priority Data

Sep. 12, 2019 (IN) .............................. 201921036803

(51) Int. Cl.
| | |
|---|---|
| C07D 207/08 | (2006.01) |
| A61K 31/40 | (2006.01) |
| A61K 31/4025 | (2006.01) |
| A61K 31/427 | (2006.01) |
| A61K 38/20 | (2006.01) |
| A61K 38/21 | (2006.01) |
| A61K 45/06 | (2006.01) |
| A61P 29/00 | (2006.01) |
| C07D 207/48 | (2006.01) |
| C07D 405/04 | (2006.01) |
| C07D 417/06 | (2006.01) |

(52) U.S. Cl.
CPC .......... *A61K 31/40* (2013.01); *A61K 31/4025* (2013.01); *A61K 31/427* (2013.01); *A61K 38/2013* (2013.01); *A61K 38/21* (2013.01); *A61K 45/06* (2013.01); *C07D 207/08* (2013.01); *C07D 207/48* (2013.01); *C07D 405/04* (2013.01); *C07D 417/06* (2013.01)

(58) Field of Classification Search
CPC .. A61K 31/40; A61K 31/4025; A61K 31/427; A61K 38/2013; A61K 38/21; A61K 45/06; C07D 207/08; C07D 207/48; C07D 405/04; C07D 417/06; Y02A 50/30; A61P 29/00
See application file for complete search history.

(56) References Cited

U.S. PATENT DOCUMENTS

| | | | | |
|---|---|---|---|---|
| 4,666,506 A | * | 5/1987 | Hillemann | ............. A01N 47/36 544/212 |
| 5,258,406 A | | 11/1993 | Toth et al. | |
| 2002/0077486 A1 | | 6/2002 | Scarborough | |
| 2023/0096220 A1 | * | 3/2023 | Sharma | ................ C07D 335/02 514/315 |

FOREIGN PATENT DOCUMENTS

| | | |
|---|---|---|
| WO | 98/32733 A1 | 7/1998 |
| WO | 2016/131098 A1 | 8/2016 |
| WO | 2018225018 A1 | 12/2018 |

OTHER PUBLICATIONS

"Sulfonimidamide Analogs of Oncolytic Sulfonylureas" JE Toth, GB Grindey, WJ Ehlhardt, JE Ray, GB Boder, JR Bewley, KK Klingerman, SBGates, SM Rinzel, RM Schultz, LC Weir, and JF Worzalla Journal of Medicinal Chemistry 1997 40 (6), 1018-1025 (Year: 1997).*
Toth, J., et al., "Sulfonimidamide Analogs of Oncolytic Sulfonylureas", Journal of Medicinal Chemistry, vol. 40, No. 6, 1997.
Database PubChem Compound [Online], Oct. 26, 2016, Retrieved from NCBI.
Database Registry [Online] Chemical Abstracts Service, Jun. 13, 2008.
PCT, International Preliminary Report On Patentability dated Aug. 12, 2021.
PCT, International Search Report dated Nov. 11, 2020.
PCT, Written Opinion International Search Authority, dated Nov. 11, 2020.
Applicant's Response to Written Opinion of International Searching Authority dated Nov. 11, 2020, Response dated Jul. 12, 2021.

* cited by examiner

*Primary Examiner* — Adam C Milligan
*Assistant Examiner* — Sophia P Hirakis
(74) *Attorney, Agent, or Firm* — IPHORGAN LTD.

(57) ABSTRACT

The present invention relates to novel heterocyclic compounds of general formula (I) their tautomers, stereoisomers, enantiomers, pharmaceutically acceptable salts and pharmaceutical composition. The compounds of general formula (I) belongs to the family of NOD like receptor family (NLR) protein NLRP3 modulators. The present invention thus relates to novel NLRP3 modulators and use of these novel inhibitor compounds in the treatment of disease or conditions as well as treatment of disease states mediated by NLRP3 as well as treatment of diseases or conditions in which interleukin 1β activity and interleukin-18 (IL-18) is implicated.

7 Claims, No Drawings

SUBSTITUTED SULFOXIMINE DERIVATIVES

CROSS REFERENCE TO RELATED APPLICATIONS

This application is a national stage completion application of PCT Application No. PCT/IB2020/058464, filed Sep. 11, 2020, and claims priority from India application No. 201921036803, filed Sep. 12, 2019. Each of these applications is incorporated by reference herein in its entirety.

FIELD OF THE INVENTION

The present invention relates to novel heterocyclic compounds of the general formula (I) their pharmaceutically acceptable salts, pharmaceutically acceptable solvates, enantiomers, diastereomers and polymorphs. The invention also relates to processes for the preparation of the compounds of invention, pharmaceutical compositions containing the compounds and their use as the compounds of the invention belong to the family of NOD-like receptor family (NLR) protein NLRP3 modulators. The present invention thus relates to novel NLRP3 modulators as well as to the use of the novel inhibitor compounds in the treatment of diseases or conditions in which interleukin 10 activity is implicated.

BACKGROUND OF THE INVENTION

The NOD-like receptor family (NLR) protein NLRP3 is an intracellular signaling molecule that senses many pathogens, environmental and host-derived factors. (Wen., et. al., Immunity. 2013; 39:432-441). Activation of NLRP3 leads to binding with apoptosis associated speck-like protein containing a CARD (ASC). ASC in turn interacts with the cysteine protease caspase-1, forming a complex termed the inflammasome. This results in the activation of caspase-1, which cleaves the pro-inflammatory cytokines IL-1β and IL-18 to their active forms and mediates a type of inflammatory cell death known as pyroptosis. Other intracellular pattern recognition receptors (PRRs) are also capable of forming inflammasomes. These include other NLR family members such as NLRP1 and NLRC4 and non-NLR PRRs such as the double-stranded DNA (dsDNA) sensors absent in melanoma 2 (AIM2) and interferon, gamma inducible protein 16 (IFI16) (Latz, et. al., Nat Rev Immunol. 2013; 13:397-411). NLRP3-dependent IL-1β processing can also be activated by an indirect, non-canonical pathway downstream of caspase-1 (Lamkanfi, et. al., Cell. 2014; 157:1013-1022).

Inflammasome components such as NLRP3, ASC and caspase-1 are expressed in immune cells in the liver including Kupffer cells, infiltrating macrophages, hepatocytes, and hepatic stellate cells. Inflammasome activation is dependent on two successive signals. Signal 1 is driven by TLR and IL-1R signaling, includes expression of component proteins including NLRP3, ASC, pro-caspase-1, pro-IL-1β, and pro-IL-18. Signal 2 is provided by danger signals (DAMPS) that during NASH development are mainly released by stressed or dying hepatocytes or via a "leaky" gut (PAMPs). This process leads to oligomerization of the inflammasome components and cleavage of pro-caspase-1, leading to the release of active pro-inflammatory cytokines.

NLRP3 inflammasome acts as a key mediator of inflammatory responses through the activation of caspase-1 leading to processing and release of the pro-inflammatory cytokines interleukin-1β (IL-1β) and interleukin-18 (IL-18). NLRP3 inflammasome is a component of the inflammatory process and its aberrant activation is pathogenic in inherited disorders such as the rare periodic fever syndrome, cryopyrin associated periodic syndromes (CAPS), Tumor necrosis factor receptor-associated periodic syndrome (TRAPS) and complex diseases such as multiple sclerosis, type 2 diabetes, atherosclerosis, asthma, gouty arthritis, IBD (Inflammatory bowl disease) and inflammatory central nervous system (CNS) diseases. (Masters, et. al., Annu Rev Immunol. 2009; 27:621-668; Strowig, et. al., Nature 2012, 481, 278-286; Guo, et. al., Nat. Med. 2015, 21, 677.)

Inflammation is an essential host response to infection and injury. The regulation of the pro-inflammatory cytokine interleukin-1β (IL-1β), which is central to host responses to infection, also causes tissue injury when activated inappropriately. (Dinarello, et. al., Nat. Rev. Drug Discovery 2012, 11, 633-652.) NLRP3 inflammasome activation plays a key role in each of the components including induction of pro-inflammatory signaling, hepatocellular injury and cell death, and activation of the hepatic stellate cells (HSC) that are responsible for collagen deposition and liver fibrosis. In particular, the transition from NAFLD to NASH associates with NLRP3-inflammasome activation and an increased expression of inflammasome-related components, including apoptosis-associated speck-like protein containing a carboxy-terminal CARD (ASC), caspase-1 (CASP-1) and pannexin. (Mridha, et. al., Journal of Hepatology, 2017, 66 (5), 1037-1046)

Current treatments for NLRP3 related diseases include biologic agents that target IL-1. These are the recombinant IL-1 receptor antagonist Anakinra, the neutralizing IL-1β antibody Canakinumab and the soluble decoy IL-1 receptor Rilonacept.

WIPO patent publication no. WO98/32733, WO2001/019390, WO2014/190015, WO2016/123229 WO2016/131098 disclosed sulfonylureas derivatives and related compounds as NLRP3 inflammasome inhibitors. WO2017/017469 disclosed certain cyclic diarylboron derivatives as NLRP3 inflammasome inhibitors for the treatment of diseases or conditions in which interleukin 1β activity is implicated. Some of the recent patent applications such as WO2017/031161, WO2017/079352, WO2017/129897, WO2017/140778, WO2017/184623 WO2018/225018, WO2019/043610, WO2019/023147, WO 2019/008025 WO2019/008029, WO2019/034696, WO2019/068772, WO2020/035464, WO2020/102576, WO2020/104657, WO2020/148619 have also disclosed certain class of compounds as NLRP3 inhibitors.

Wipo patent publication no. WO98/32733, WO2001/019390, WO2014/190015, WO2016/123229 WO2016/131098 disclosed sulfonylureas derivatives and related compounds as NLRP3 inflammasome inhibitors.

We herein disclose novel heterocyclic compounds of general formula (I) which are NLRP3 modulators for the prevention and treatment of disease states mediated by NLRP3 or conditions in which interleukin 1β activity is implicated, including inflammation, Cryopyrin-associated periodic syndrome (CAPS), gouty arthritis, multiple sclerosis, Inflammatory bowel disease (IBD), type 2 diabetes, atherosclerosis, liver fibrosis inflammatory central nervous system (CNS) diseases like Parkinson's, Alzheimer's and other brain diseases, mediated via NLRP3 pathway. More particularly, embodiments of the present invention are useful as therapeutics in the treatment of a variety of pathological conditions including (but not limited to) lymphoma, autoimmune diseases, heteroimmune diseases, inflammatory diseases, cancer, and neurodegenerative diseases or conditions. Furthermore, suppression of IL-1β and IL-18 using NLRP3 inflammasome inhibitors would be an effective therapy during a cytokine storm and might be a plausible treatment option for diseases like severe acute respiratory syndrome (SARS), Middle East respiratory syndrome (MERS), Spanish flu, COVID19 (Coronavirus disease 2019), hepatitis C virus, chikungunya virus, influenza A virus, herpes simplex virus type 1 and Japanese encephalitis virus, where high levels of interleukin (IL)-1β and/or IL-18 have been associated with inflammation and Pathogenesis (Lancet 2020, 395, (10223), 497-506).

SUMMARY OF THE INVENTION

The present invention discloses heterocyclic compounds as defined by the general formula (I) that are NLRP3 modulators for the prevention and treatment of disease states mediated by NLRP3 as well as treatment of diseases or conditions in which interleukin 1β activity is implicated. The compounds of the present invention are useful in the treatment of human or animal body, by inhibition of NLRP3. The compounds of the present invention are therefore suitable for the prevention and treatment of disease states mediated by NLRP3.

Embodiment(s) of the Invention

An embodiment of the present invention provides novel heterocyclic compounds represented by the general formula (1), their tautomeric forms, their enantiomers, their diastereomers, their stereoisomers, their pharmaceutically acceptable salts and pharmaceutical compositions containing them or their mixtures thereof.

In a further embodiment of the present invention is provided pharmaceutical compositions containing compounds of the general formula (I), their tautomeric forms, their enantiomers, their diastereomers, their stereoisomers, their pharmaceutically acceptable salts, or their mixtures in combination with suitable carriers, solvents, diluents and other media normally employed in preparing such compositions.

In a still further embodiment is provided a process for preparing the novel compounds of the present invention.

DETAIL DESCRIPTION OF THE INVENTION

Accordingly, the present invention relates to the compound of general formula (I)

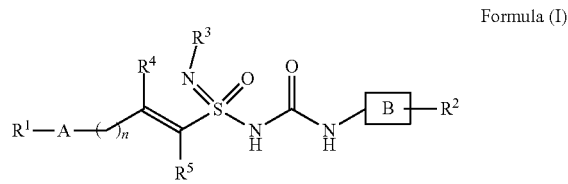

Formula (I)

their tautomeric forms, their stereoisomers, their enantiomers, their pharmaceutically acceptable salts, and pharmaceutical compositions containing them wherein 'A' represents unsubstituted or substituted group selected from $(C_1-C_6)$alkyl, $(C_2-C_6)$alkenyl, $(C_3-C_8)$cycloalkyl, aryl, heteroaryl and heterocyclyl groups each of which may optionally be further substituted with one or more than one heteroatoms;

$R^1$ is selected from one or more substituents on 'A' at each occurrence independently represents hydrogen, halogen, haloalkyl, cyano, optionally substituted groups selected from $(C_1-C_6)$alkyl, $(C_2-C_6)$alkenyl, $(C_1-C_6)$alkoxy, $(C_3-C_6)$cycloalkyl, $CO(O)(C_1-C_6)$alkyl, aryl, heteroaryl, heterocyclyl, benzyl, thiol, $(C_1-C_6)$mercapto alkyl, sulfur and its oxidized forms, $C_1-C_6$(thio-alkoxy), bridged or spiro ring systems having optionally one or more than one heteroatoms;

In an embodiment when 'A' represents ring, $R^1$ at each occurrence may represents one or more substituents selected from hydrogen, halogen, haloalkyl, cyano, optionally substituted groups selected from $(C_1-C_6)$alkyl, $(C_2-C_6)$alkenyl, $(C_1-C_6)$alkoxy, $(C_1-C_6)$mercaptoalkyl, $(C_3-C_6)$cyclalkyl, $CO(O)(C_1-C_6)$alkyl, aryl, heteroaryl, heterocyclyl, benzyl, thiol, sulfur and its oxidized forms, $C_1-C_6$(thio-alkoxy), bridged or spiro ring system having optionally one or more than one heteroatoms;

'B' represents optionally substituted $(C_3-C_6)$cycloalkyl, aryl, heteroaryl or heterocyclyl groups;

In a preferred embodiment, 'B' is selected from following ring system

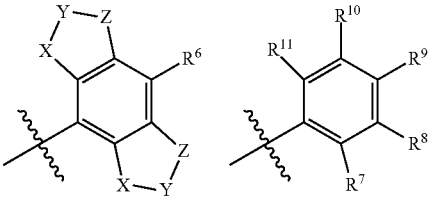

wherein X, Y, Z at each occurrence is independently selected from C, N, S, $SO_2$, and O, which may be optionally substituted;

$R^2$ at each occurrence independently represents hydrogen, halogen, cyano, optionally substituted groups selected from $(C_1-C_6)$alkyl, $(C_2-C_6)$alkenyl, $(C_1-C_6)$alkoxy $(C_3-C_6)$cycloalkyl, benzyl, aryl, heteroaryl, heterocyclyl, thiol, thioalkyl, sulfur and its oxidized forms, thioalkoxy, bridged or spiro ring system having optionally one or more than one heteroatoms;

n=0-3;

$R^3$ at each occurrence independently represents hydrogen, hydroxyl, halogen, nitro, cyano, haloalkyl, optionally substituted groups selected from $(C_1-C_{10})$alkyl, $(C_1-C_{10})$alkoxy, $(C_3-C_{10})$cycloalkyl, $(C_2-C_{10})$alkenyl, $(C_2-C_{10})$alkynyl, $SO_2(C_1-C_6)$alkyl, thiol, thioalkyl, thioalkoxy, benzyl, aryl, heteroaryl, heterocyclyl group having optionally one or more than one heteroatoms; Alternatively $R^3$ and $R^4$ or $R^3$ and $R^5$ together with the atom to which they are attached may form an optionally substituted 4 to 8 membered heterocyclic ring system having optionally one or more than one heteroatoms;

Each of $R^4$, $R^5$, $R^6$, $R^7$, $R^8$, $R^9$, $R^{10}$ and $R^{11}$ at each occurrence are independently selected from hydrogen, halogen, cyano, amide, sulphonamide, acyl, alkyl, branched alkyl, hydroxyl, optionally substituted groups selected from $(C_1-C_6)$alkyl, $(C_1-C_6)$haloalkyl, $(C_3-C_6)$cycloalkyl, $(C_1-C_6)$alkoxy, benzyl, aryl, heteroaryl, heterocyclyl; Alternatively, $R^4$ and $R^5$ may form a bond; Alternatively, $R^4$ and 'A' together with the atom to which they are attached may form an optionally substituted 4 to 8 membered heterocyclic ring system having optionally one or more than one heteroatoms;

Alternatively each of $R^7$ and $R^8$, $R^8$ and $R^9$, $R^9$ and $R^{10}$ or $R^{10}$ and $R^{11}$ wherever possible, together may form a 4 to 7 membered saturated or partially saturated ring containing from 0-2 additional heteroatoms selected from the group consisting of N, O, and $S(O)_p$; p=1-2.

When any of above defined group is substituted the substitutions on them may be selected from those described above or may additionally be selected from hydrogen, hydroxy, cyano, halo, haloalkyl, haloalkyloxy, alkylthio $(C_1-C_6)$alkyl, $(C_2-C_6)$alkenyl, $(C_2-C_6)$alkynyl, $(C_3-C_7)$cycloalkyl, $(C_1-C_6)$alkoxy, —$COR_{12}$, —$CSR_{12}$, $C(O)OR_{12}$, $C(O)$—$R_{12}$, —$C(O)$—$NR_{12}R_{13}$, —$C(S)$—$NR_{12}R_{13}$, —$SO_2R_{12}$ group, wherein each of $R_{12}$ and $R_{13}$ is independently selected from hydrogen, optionally substituted group selected from $(C_1-C_6)$alkyl, $(C_2-C_6)$alkenyl, $(C_2-C_6)$alkynyl, $(C_3-C_7)$cycloalkyl, aryl, heteroaryl, heterocyclyl groups;

In a preferred embodiment, $R^1$ at each occurrence is selected from hydrogen, halogen, haloalkyl, optionally unsubstituted or substituted groups selected from $(C_1-C_6)$alkyl, $(C_3-C_6)$cycloalkyl, $CO(O)(C_1-C_6)$alkyl, aryl, heterocyclyl, thiol, $(C_1-C_6)$mercapto alkyl, sulfur and its oxidized forms, $C_1-C_6$(thio-alkoxy);

In a preferred embodiment, $R^2$ at each occurrence is selected from hydrogen, halogen, haloalkyl, optionally substituted groups selected from $(C_1-C_6)$alkyl;

In a preferred embodiment, $R^3$ is selected from groups hydrogen and cyano, optionally substituted group selected from $(C_1-C_6)$alkyl;

In a preferred embodiment each of $R^4$, $R^5$, $R^6$, $R^7$, $R^8$, $R^9$, $R^{10}$ and $R^{11}$ at each occurrence independently represents hydrogen, halogen, haloalkyl, optionally substituted groups selected from $(C_1-C_6)$alkyl;

In a preferred embodiment, the groups, radicals described above may be selected from:

"Alkyl", as well as other groups having the prefix "alk", such as alkoxy and alkanoyl, means a carbon chain which may further be substituted with an oxygen atom as is well understood by a skilled artisan, which may further be either linear or branched, and combinations thereof, unless the carbon chain is defined otherwise. Examples of alkyl group include but are not limited to methyl, ethyl, propyl, isopropyl, butyl, sec-butyl, tert.-butyl, pentyl, hexyl etc. Where the specified number of carbon atoms permits e.g. from $C_{(3-10)}$, the term alkyl also includes cycloalkyl groups, and combinations of linear or branched alkyl chains combined with cycloalkyl structures. When no number of carbon atoms is specified, $C_{(1-6)}$ is intended. "Alkenyl" means carbon chains which contain at least one carbon-carbon double bond, and which may be linear or branched or combinations thereof, unless the carbon chain is defined otherwise. Examples of alkenyl include but not limited to vinyl, allyl, isopropenyl, hexenyl, pentenyl, heptenyl, 1-propenyl, 2-butenyl, 2-methyl-2-butenyl etc. Where the specified number of carbon atoms permits, e.g., from $C_{(5-10)}$, the term alkenyl also includes cycloalkenyl groups and combinations of linear, branched and cyclic structures. When no number of carbon atoms is specified, $C_{(2-6)}$ is intended.

"Alkynyl" means carbon chains which contain at least one carbon-carbon triple bond, and which may be linear or branched or combinations thereof. Examples of alkynyl include ethynyl, propargyl, 3-methyl-1-pentynyl etc. When no number of carbon atoms specified, is intended.

The "thioalkyl" group used either alone or in combination with other radicals, denotes an alkyl group, as defined above, attached to a group of formula —SR', where R' represents hydrogen, alkyl or aryl group, e.g. thiomethyl, methylthiomethyl, phenylthiomethyl and the like, which may be optionally substituted.

As used herein, "carbocycle" or "carbocyclic residue" is intended to mean any stable monocyclic or bicyclic or tricyclic ring, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). In a broader perspective, the term carbocycle is intended to include, wherever applicable, the groups representing cycloalkyl, phenyl and other saturated, partially saturated or aromatic residues;

"Cycloalkyl" is the subset of alkyl and means saturated carbocyclic ring having a specified number of carbon atoms, preferably 3-6 carbon atoms. Examples of cycloalkyl include cyclopropyl, cyclobutyl, cyclopentyl, cyclohexyl, cycloheptyl etc. A cycloalkyl group generally is monocyclic unless otherwise stated. In a preferred embodiment cycloalkyl groups are saturated unless and otherwise stated.

The term "alkoxy" refers to the straight or branched chain alkoxides of the number of carbon atoms specified.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls.

"Heterocyclyl" means a saturated, partially saturated or unsaturated aromatic or non-aromatic mono, bi or tricyclic radicals, containing one or more heteroatoms selected from nitrogen, sulfur and oxygen, further optionally including the oxidized forms of sulfur, namely SO & $SO_2$. Examples of heterocycles include tetrahydrofuran (THF), dihydrofuran, 1,4-dioxane, morpholine, 1,4-dithiane, piperazine, piperidine, 1,3-dioxolane, imidazoline, imidazolidine, pyrrolidine, pyrroline, tetrahydropyran, dihydropyran, oxathiolane, dithiolane, 1,3-dioxane, 1,3-dithiane, oxathiane, thiomorpholine, etc. The term "heterocycloalkyl" refers to a heterocyclic group as defined above connected to an alkyl group as defined above; "Heteroaryl" means an aromatic or partially aromatic heterocycle that contains at least one ring heteroatom selected from O, S and N. Heteroaryls thus include heteroaryls fused to other kinds of rings, such as aryls, cycloalkyls, and heterocycles that are not aromatic. Examples of heteroaryl groups include; pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzthiazolyl, benzothiadiazolyl, dihydrobenzofuranyl, indolinyl, pyridazinyl, indazolyl, isoindolyl, dihydrobenzothienyl, indolinyl, pyridazinyl, indazolyl, isoindolyl, dihydrobenzothienyl, indolizinyl, cinnolinyl, phthalazinyl, quinazolinyl, napthyridinyl, carbazolyl, benzodioxolyl, quinoxalinyl, purinyl, furazanyl, isobenzylfuranyl, benzimidazolyl, benzofuranyt, benzothienyl, quinolyl, indolyl, isoquinolyl, dibenzofuranyl etc. For heterocyclyl; and heteroaryl groups, rings and ring systems containing from 3-15 carbon atoms are included, forming 1-3 rings.

The term "haloalkyl" means an alkyl structure in which at least one hydrogen is replaced with a halogen atom. In certain embodiments in which two or more hydrogen atoms are replaced with halogen atoms, the halogen atoms are all the same as one another.

The "haloalkoxy" group is selected from suitable haloalkyl, as defined above, directly attached to an oxygen atom, more preferably groups selected from fluoromethoxy, chloromethoxy, fluoroethoxy, chloroethoxy and the like;

In certain other embodiment in which two or more hydrogen atoms are replaced with halogen atoms, the halogen atoms are not all the same as one another.

"Aryloxyalkyl" means an alkyl radical substituted with aryloxy group as defined herein.

"Aryloxyaryl" means an aryl radical substituted with aryloxy group as defined herein.

"Aryloxyheteroaryl" means a heteroaryl radical substituted with aryloxy group as defined herein.

"Halo/Halogen" refers to fluorine, chlorine, bromine, iodine. Chlorine and fluorine are generally preferred.

Suitable groups and substituents on the groups may be selected from those described anywhere in the specification.

The term "substituted," as used herein, means that any one or more hydrogen on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. Such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromie, hydrochloric, hydroiodide, hydroxymaleic, hydroxynaphthoic, isethionic, lactic, lactobionic, -lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The term 'optional' or 'optionally' means that the subsequent described event or circumstance may or may not occur, and the description includes instances where the event or circumstance occur and instances in which it does not. For example, optionally substituted alkyl' means either 'alkyl' or 'substituted alkyl'. Further an optionally substituted group includes an unsubstituted group.

Unless otherwise stated in the specification, structures depicted herein are also meant to include compounds which differ only in the presence of one or more isotopically enriched atoms.

Particularly useful compounds may be selected from but not limited to the following:

tert-butyl (2R)-2-((E)-2-(N-((1,2,3,5,6,7-hexahydro-s-indacen-4-yl)carbamoyl)sulfamidimidoyl)vinyl)pyrrolidine-1-carboxylate;

tert-butyl (2S)-2-((E)-2-(N-((1,2,3,5,6,7-hexahydro-s-indacen-4-yl)carbamoyl)sulfamidimidoyl)vinyl)-2-methylpyrrolidine-1-carboxylate;

tert-butyl (2S)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxylate;

(E)-N'-cyano-N-((1,2,3,5,6,7-hexahydro-s-indacen-4-yl)carbamoyl)-2-((S)-2-methylpyrrolidin-2-yl)ethene-1-sulfonimidamide hydrochloride;

(E)-2-((S)-1,2-dimethylpyrrolidin-2-yl)-N-((1,2,3,5,6,7-hexahydro-s-indacen-4-yl)carbamoyl)ethene-1-sulfonimidamide;

(E)-2-((S)-1,2-dimethylpyrrolidin-2-yl)-N-((1,2,3,5,6,7-hexahydro-s-indacen-4-yl)carbamoyl)-N'-methylethene-1-sulfonimidamide;

(E)-N'-cyano-2-((S)-1,2-dimethylpyrrolidin-2-yl)-N-((1,2,3,5,6,7-hexahydro-s-indacen-4-yl)carbamoyl)ethene-1-sulfonimidamide;

(E)-N'-cyano-2-((R)-1-(cyclohexylsulfonyl)pyrrolidin-2-yl)-N-((1,2,3,5,6,7-hexahydro-s-indacen-4-yl)carbamoyl)ethene-1-sulfonimidamide;

(E)-N'-cyano-2-((R)-1-((2-cyanophenyl)sulfonyl)pyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((R)-pyrrolidin-2-yl)ethene-1-sulfonimidamide hydrochloride;

(E)-N'-cyano-N-((1,2,3,5,6,7-hexahydro-s-indacen-4-yl)carbamoyl)-2-((R)-1-methylpyrrolidin-2-yl)ethene-1-sulfonimidamide;

tert-butyl (2R)-2-((E)-2-(N-((1,2,3,5,6,7-hexahydro-s-indacen-4-yl)carbamoyl)sulfamidimidoyl)vinyl)-2-methylpyrrolidine-1-carboxylate;

tert-butyl (2R)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxylate;

(E)-N'-cyano-N-((1,2,3,5,6,7-hexahydro-s-indacen-4-yl)carbamoyl)-2-((R)-2-methylpyrrolidin-2-yl)ethene-1-sulfonimidamide hydrochloride;

(E)-N'-cyano-2-((R)-1,2-dimethylpyrrolidin-2-yl)-N-((1,2,3,5,6,7-hexahydro-s-indacen-4-yl)carbamoyl)ethene-1-sulfonimidamide;

tert-butyl (2-((2S)-2-((E)-2-(N'-cyano-N-((1,2,3,5,6,7-hexahydro-s-indacen-4-yl)carbamoyl)sulfamidimidoyl)vinyl)-2-methylpyrrolidin-1-yl)ethyl)(methyl)carbamate;

(E)-N'-cyano-N-((1,2,3,5,6,7-hexahydro-s-indacen-4-yl)carbamoyl)-2-((S)-1-isopropyl-2-methylpyrrolidin-2-yl)ethene-1-sulfonimidamide;

(E)-N'-cyano-2-((S)-1-cyclopentyl-2-methylpyrrolidin-2-yl)-N-((1,2,3,5,6,7-hexahydro-s-indacen-4-yl)carbamoyl)ethene-1-sulfonimidamide;

(E)-N'-cyano-2-((S)-1-cyclobutyl-2-methylpyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((S)-2-methylpyrrolidin-2-yl)ethene-1-sulfonimidamide;

(E)-N'-cyano-2-((S)-1-(cyclopropylmethyl)-2-methylpyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((S)-2-methylpyrrolidin-2-yl)ethene-1-sulfonimidamide 2,2,2-trifluoroacetate;

(E)-N'-cyano-N-((1,2,3,5,6,7-hexahydro-s-indacen-4-yl)carbamoyl)-2-((S)-2-methyl-1-(tetrahydro-2H-pyran-4-yl)pyrrolidin-2-yl)ethene-1-sulfonimidamide;

(E)-N'-cyano-N-((1,2,3,5,6,7-hexahydro-s-indacen-4-yl)carbamoyl)-2-((S)-1-isobutyl-2-methylpyrrolidin-2-yl)ethene-1-sulfonimidamide;

(E)-2-((S)-1-acetyl-2-methylpyrrolidin-2-yl)-N'-cyano-N-((1,2,3,5,6,7-hexahydro-s-indacen-4-yl)carbamoyl)ethene-1-sulfonimidamide;

(E)-N'-cyano-2-((S)-1-ethyl-2-methylpyrrolidin-2-yl)-N-((1,2,3,5,6,7-hexahydro-s-indacen-4-yl)carbamoyl)ethene-1-sulfonimidamide;

(E)-N'-cyano-2-((S)-1-cyclohexyl-2-methylpyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((S)-1-(2-methoxyethyl)-2-methylpyrrolidin-2-yl)ethene-1-sulfonimidamide;

(E)-N'-cyano-N-((1,2,3,5,6,7-hexahydro-s-indacen-4-yl)carbamoyl)-2-((S)-2-methyl-1-(thiazol-2-ylmethyl)pyrrolidin-2-yl)ethene-1-sulfonimidamide;

(E)-N'-cyano-N-((1,2,3,5,6,7-hexahydro-s-indacen-4-yl)carbamoyl)-2-((S)-2-methyl-1-(2-methyl-2-(pyrrolidin-1-yl)propyl)pyrrolidin-2-yl)ethene-1-sulfonimidamide;

(2S)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxamide;

sodium ((E)-N-cyano-2-((S)-1-1sobutyl-2-methylpyrrolidin-2-yl)vinylsulfonimidoyl)((1,2,3,5,6,7-hexahydro-s-indacen-4-yl)carbamoyl)amide;

sodium ((E)-N-cyano-2-((S)-1-cyclohexyl-2-methyl pyrrolidin-2-yl)vinyl sulfonimidoyl)((1,2,3,5,6,7-hexahydro-s-indacen-4-yl)carbamoyl)amide;

tert-butyl (2R)-2-((E)-2-(N'-cyano-N-((1,2,3,5,6,7-hexahydro-s-indacen-4-yl)carbamoyl)sulfamidimidoyl)vinyl)pyrrolidine-1-carboxylate;

(E)-N-((1,2,3,5,6,7-hexahydro-s-indacen-4-yl)carbamoyl)-N'-methyl-2-((R)-pyrrolidin-2-yl)ethene-1-sulfonimidamide 2,2,2-trifluoroacetate;

(E)-2-((S)-1,2-dimethylpyrrolidin-2-yl)-N-((1,2,3,5,6,7-hexahydro-s-indacen-4-yl)carbamoyl)-N'-methylethene-1-sulfonimidamide;

tert-butyl (2R)-2-((E)-2-(N-((1,2,3,5,6,7-hexahydro-s-indacen-4-yl)carbamoyl)sulfamidimidoyl)vinyl)pyrrolidine-1-carboxylate;

(E)-N'-cyano-2-((R)-1-(cyclohexylsulfonyl)pyrrolidin-2-yl)-N-((1,2,3,5,6,7-hexahydro-s-indacen-4-yl)carbamoyl)ethene-1-sulfonimidamide;

(E)-N'-cyano-2-((R)-1-((2-cyanophenyl)sulfonyl)pyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((R)-1-methylpyrrolidin-2-yl)ethene-1-sulfonimidamide;

(E)-N-((1,2,3,5,6,7-hexahydro-s-indacen-4-yl)carbamoyl)-2-((R)-1-methylpyrrolidin-2-yl)ethene-1-sulfonimidamide;

(E)-N'-cyano-2-((R)-1-ethylpyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((R)-1-isopropylpyrrolidin-2-yl)ethene-1-sulfonimidamide;

(E)-N'-cyano-2-((R)-1-(cyclopropylmethyl)pyrrolidin-2-yl)-N-((1,2,3,5,6,7-hexahydro-s-indacen-4-yl)carbamoyl)ethene-1-sulfonimidamide;

(E)-N'-cyano-2-((S)-1-(cyclopropylmethyl)pyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((S)-1-methylpyrrolidin-2-yl)ethene-1-sulfonimidamide;

(E)-N'-cyano-N-((1,2,3,5,6,7-hexahydro-s-indacen-4-yl)carbamoyl)-2-((R)-1-(methylsulfonyl)pyrrolidin-2-yl)ethene-1-sulfonimidamide;

(E)-N'-cyano-2-((R)-1-(ethylsulfonyl)pyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((S)-1-(oxetan-3-yl)pyrrolidin-2-yl)ethene-1-sulfonimidamide;

(E)-N'-cyano-N-((1,2,3,5,6,7-hexahydro-s-indacen-4-yl)carbamoyl)-2-((R)-1-propionylpyrrolidin-2-yl)ethene-1-sulfonimidamide;

(E)-2-((R)-1-acetylpyrrolidin-2-yl)-N'-cyano-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-(thiazol-2-yl)ethene-1-sulfonimidamide;

(E)-N'-cyano-N-((1,2,3,5,6,7-hexahydro-s-indacen-4-yl)carbamoyl)-2-(thiophen-2-yl)ethene-1-sulfonimidamide;

(E)-N'-cyano-N-((1,2,3,5,6,7-hexahydro-s-indacen-4-yl)carbamoyl)-2-phenylethene-1-sulfonimidamide;

(E)-N'-cyano-N-((1,2,3,5,6,7-hexahydro-s-indacen-4-yl)carbamoyl)-2-((S)-2-methyl-1-(oxetan-3-yl)pyrrolidin-2-yl)ethene-1-sulfonimidamide;

(E)-N'-cyano-N-((1,2,3,5,6,7-hexahydro-s-indacen-4-yl)carbamoyl)-2-((S)-1-isopropyl-2-methylpyrrolidin-2-yl)ethene-1-sulfonimidamide;

(E)-N'-cyano-2-((S)-1,2-dimethylpyrrolidin-2-yl)-N-((1,2,3,5,6,7-hexahydro-s-indacen-4-yl)carbamoyl)ethene-1-sulfonimidamide;

(E)-N'-cyano-2-((R)-1-(cyclohexylsulfonyl)-2-methylpyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((R)-2-methyl-1-(methylsulfonyl)pyrrolidin-2-yl)ethene-1-sulfonimidamide;

(E)-2-((R)-1-acetyl-2-methylpyrrolidin-2-yl)-N'-cyano-N-((1,2,3,5,6,7-hexahydro-s-indacen-4-yl)carbamoyl)ethene-1-sulfonimidamide;

(E)-N'-cyano-2-((R)-1,2-dimethylpyrrolidin-2-yl)-N-((1,2,3,5-tetrahydro-s-indacen-4-yl)carbamoyl)ethene-1-sulfonimidamide;

(E)-N'-cyano-2-((R)-1,2-dimethylpyrrolidin-2-yl)-N-((1,2,3,7-tetrahydro-s-indacen-4-yl)carbamoyl)ethene-1-sulfonimidamide;

(E)-N'-cyano-2-((R)-1,2-dimethyl-2,5-dihydro-1H-pyrrol-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((R)-2-methyl-1-(methyl-d3)pyrrolidin-2-yl)ethene-1-sulfonimidamide;

(E)-N'-cyano-N-((1,2,3,5,6,7-hexahydro-s-indacen-4-yl)carbamoyl)-2-((R)-1-(methyl-d3)pyrrolidin-2-yl)ethene-1-sulfonimidamide;

(E)-N'-cyano-N-((1,2,3,5,6,7-hexahydro-s-indacen-4-yl)carbamoyl)-2-((S)-1-(methyl-d3)pyrrolidin-2-yl)ethene-1-sulfonimidamide;

(E)-N'-cyano-N-((1,2,3,5,6,7-hexahydro-s-indacen-4-yl)carbamoyl)-2-((S)-2-methyl-1-(methyl-d3)pyrrolidin-2-yl)ethene-1-sulfonimidamide;

(E)-N-((1,2,3,5,6,7-hexahydro-s-indacen-4-yl)carbamoyl)-2-((S)-2-methyl-1-(methyl-d3)pyrrolidin-2-yl)ethene-1-sulfonimidamide;

(E)-N-((1,2,3,5,6,7-hexahydro-s-indacen-4-yl)carbamoyl)-2-((S)-1-(methyl-d3)pyrrolidin-2-yl)ethene-1-sulfonimidamide;

(E)-N-((1,2,3,5,6,7-hexahydro-s-indacen-4-yl)carbamoyl)-2-((R)-1-(methyl-d3)pyrrolidin-2-yl)ethene-1-sulfonimidamide;

(E)-N'-cyano-3-(((S)-1,2-dimethylpyrrolidin-2-yl)methoxy)-N-((1,2,3,5,6,7-hexahydro-s-indacen-4-yl)carbamoyl)prop-1-ene-1-sulfonimidamide;

(E)-3-(((S)-1,2-dimethylpyrrolidin-2-yl)methoxy)-N-((1,2,3,5,6,7-hexahydro-s-indacen-4-yl)carbamoyl)prop-1-ene-1-sulfonimidamide;

(E)-N'-cyano-2-(((S)-1,2-dimethylpyrrolidin-2-yl)methoxy)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-(2-methylisoindolin-1-yl)ethene-1-sulfonimidamide;

(E)-N'-cyano-N-((1,2,3,5,6,7-hexahydro-s-indacen-4-yl)carbamoyl)-2-(isoindolin-1-yl)ethene-1-sulfonimidamide;

(E)-N'-cyano-2-(1,3-dihydroisobenzofuran-1-yl)-N-((1,2,3,5,6,7-hexahydro-s-indacen-4-yl)carbamoyl)ethene-1-sulfonimidamide;

(E)-N'-cyano-2-(1,3-dihydrobenzo[c]thiophen-1-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-(2-methyloctahydrocyclopenta[c]pyrrol-1-yl)ethene-1-sulfonimidamide;

(E)-N'-cyano-N-((1,2,3,5,6,7-hexahydro-s-indacen-4-yl)carbamoyl)-2-(octahydrocyclopenta[c]pyrrol-1-yl)ethene-1-sulfonimidamide;

(E)-N'-cyano-2-(hexahydro-1H-cyclopenta[c]furan-1-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-(5-methylhexahydro-1H-furo[3,4-c]pyrrol-1-yl)ethene-1-sulfonimidamide;

(E)-N'-cyano-N-((1,2,3,5,6,7-hexahydro-s-indacen-4-yl)carbamoyl)-2-(5-methylhexahydro-1H-212-pyrrolo[3,4-c]pyrrol-1-yl)ethene-1-sulfonimidamide;

(E)-N'-cyano-2-(2,5-dimethyloctahydropyrrolo[3,4-c]pyrrol-1-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((R)-1-isobutoxy-2-methylpyrrolidin-2-yl)ethene-1-sulfonimidamide;

(E)-N'-cyano-N-((1,2,3,5,6,7-hexahydro-s-indacen-4-yl)carbamoyl)-2-(2-methyloctahydrocyclopenta[c]pyrrol-5-yl)ethene-1-sulfonimidamide;

(E)-N-((1,2,3,5,6,7-hexahydro-s-indacen-4-yl)carbamoyl)-2-(2-methyloctahydrocyclopenta[c]pyrrol-5-yl)ethene-1-sulfonimidamide;

(E)-N'-cyano-2-(hexahydro-1H-cyclopenta[c]furan-5-yl)-N-((1,2,3,5,6,7-hexahydro-s-indacen-4-yl)carbamoyl)ethene-1-sulfonimidamide;

(E)-N'-cyano-2-(hexahydro-1H-cyclopenta[c]thiophen-5-yl)-N-((1,2,3,5,6,7-hexahydro-s-indacen-4-yl)carbamoyl)ethene-1-sulfonimidamide;

Sodium((E)-N-cyano-2-((R)-1-(methyl-d3)pyrrolidin-2-yl)vinylsulfonimidoyl)((1,2,3,5,6,7-hexahydro-s-indacen-4-yl)carbamoyl)amide;

N-((E)-N-cyano-2-((R)-1,2-dimethylpyrrolidin-2-yl)vinylsulfonimidoyl)-2-(1,2,3,5,6,7-hexahydro-s-indacen-4-yl)acetamide;

N-((E)-N-cyano-2-((S)-1-isopropyl-2-methylpyrrolidin-2-yl)vinylsulfonimidoyl)-2-(1,2,3,5,6,7-hexahydro-s-indacen-4-yl)acetamide;

1-(1,2,3,5,6,7-hexahydro-s-indacen-4-yl)-3-(4-((1-methylpyrrolidin-2-yl)methyl)-1-oxido-3-oxo-isothiazolidin-1-ylidene) urea;

1-(4-((R)-1,2-dimethylpyrrolidin-2-yl)methyl)-1-oxido-3-oxo-isothiazolidin-1-ylidene)-3-(1,2,3,5,6,7-hexahydro-s-indacen-4-yl) urea;

1-(4-(((R)-1,2-dimethylpyrrolidin-2-yl)methyl)-1-oxido-3-oxo-4,5-dihydro-3H-isothiazol-1-yl)-3-(1,2,3,5,6,7-hexahydro-s-indacen-4-yl) urea;

(E)-N'-cyano-N-((2,6-diisopropylphenyl)carbamoyl)-2-((S)-1-isopropyl-2-methylpyrrolidin-2-yl)ethene-1-sulfonimidamide;

(E)-N'-cyano-2-((S)-1-isopropyl-2-methylpyrrolidin-2-yl)-N-((5-methyl-2,3-dihydro-1H-inden-4-yl)carbamoyl)ethene-1-sulfonimidamide;

(E)-N'-cyano-N-((4-fluoro-2,6-diisopropylphenyl)carbamoyl)-2-((S)-1-isopropyl-2-methylpyrrolidin-2-yl)ethene-1-sulfonimidamide;

(E)-N'-cyano-2-((S)-1,2-dimethylpyrrolidin-2-yl)-N-((1,2,3,5,6,7-hexahydrodicyclopenta[b,e]pyridin-8-yl)carbamoyl)ethene-1-sulfonimidamide;

(E)-N'-cyano-2-((S)-1,2-dimethylpyrrolidin-2-yl)-N-((3-methyl-1,2,3,5,6,7-hexahydrodicyclopenta[b,e]pyridin-8-yl)carbamoyl)ethene-1-sulfonimidamide;

1-15-(R)-1,2-dimethylpyrrolidin-2-yl)methyl)-1-oxido-3-oxo-3,4,5,6-tetrahydro-2-thiazin-1-yl)-3-(1,2,3,5,6,7-hexahydro-s-indacen-4-yl) urea;

1-(5-((R)-1,2-dimethylpyrrolidin-2-yl)methyl)-1-oxido-3-oxo-2-thiazinan-1-ylidene)-3-(1,2,3,5,6,7-hexahydro-s-indacen-4-yl) urea; 1-((5S)-5-((R)-1,2-dimethylpyrrolidin-2-yl)-1-oxido-3-oxo-2-thiazinan-1-ylidene)-3-(1,2,3,5,6,7-hexahydro-s-indacen-4-yl) urea;

or pharmaceutically acceptable salts of any of the compounds above.

Following is a list of abbreviations used in the description of the preparation of the compounds of the present invention:

bs: broad singlet
$CDCl_3$: Deuterated chloroform
$CHCl_3$: Chloroform
d: doublet
dd: doublet of doublet
dt: doublet of triplet
DCM: Dichloromethane
DMAC: N,N-(Dimethylacetamide)
DMAP: 4-(Dimethylamino) pyridine
DMF: N,N-Dimethyl formamide
DMSO: Dimethyl sulfoxide
EDTA: Ethylenediaminetertraacetic acid
EtOAc: Ethyl acetate
EtOH: Ethanol
HCl(g): Hydrogen chloride (gas)
$K_2CO_3$: Potassium carbonate
MeOH: Methanol
m: multiplet
mmol: millimoles
μg: microgram
MS: Mass spectrum
$Na_2CO_3$: Sodium carbonate
ng: nanogram
NIS: N-iodosuccinimide
$^1$H NMR: Proton nuclear magnetic resonance
$POCl_3$: Phosphorylchloride
s: singlet
t: Triplet
td: triplet of doublet
THF: Tetrahydrofuran
TLC: Thin layer chromatography
RT: room temperature
$N_2$: Nitrogen PMA=Phorbol 12-myristate 13-acetate IL1β: Interleukin 1 beta TNF α: Tumor necrosis factor alpha DAMP: damage-associated molecular pattern;

PAMP: pathogen-associated molecular pattern;

TLR: Toll-like receptor.

General Process for Preparation

The novel compounds of the present invention can be prepared using the reactions and techniques described below, together with conventional techniques known to those skilled in the art of organic synthesis, or variations thereon as appreciated by those skilled in the art.

The reactions can be performed in solvents appropriate to the reagents and materials employed and suitable for the transformations being affected. Preferred methods include, but not limited to those described below, where all symbols are as defined earlier unless and otherwise defined below.

The compounds of the general formula (I) can be prepared as described in schemes below along with suitable modifications/variations which are well within the scope of a person skilled in the art.

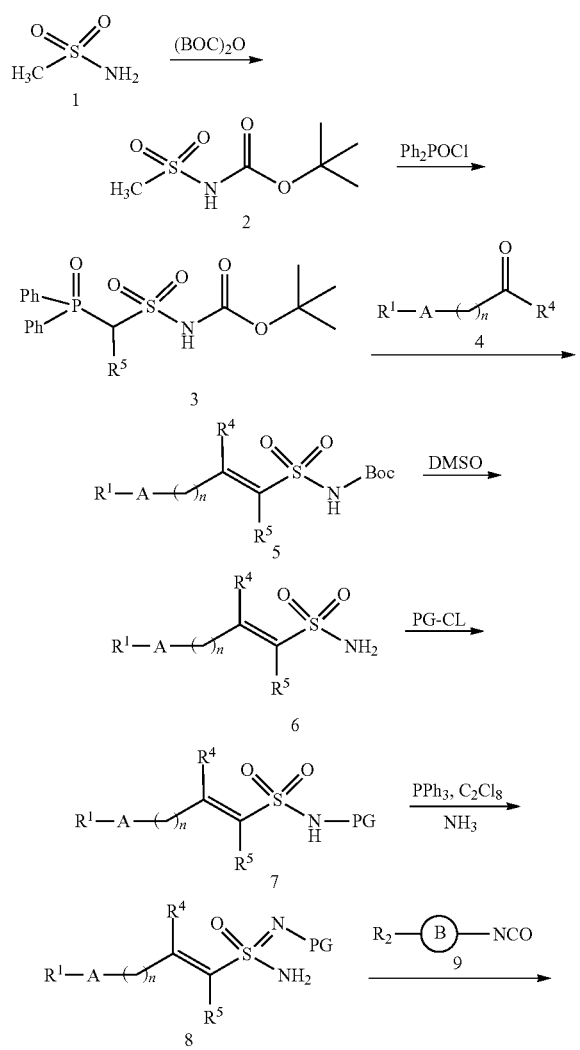

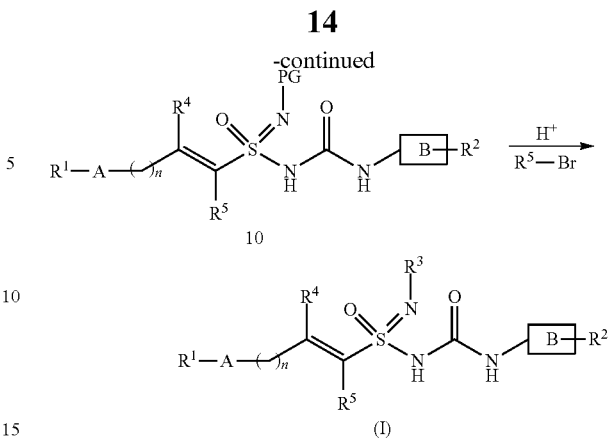

Wherein PG is selected from silyl groups like tert-butyldiphenylsilyl, tert-butyldimethylsilyl, trimethylsilyl or 9-Fluorenylmethyl carbamate, Fmoc (Fluorenylmethyloxycarbonyl), t-Butyl carbamate, Boc anhydride; Benzyl carbamate, Acetamide, Benzylamine, p-Toluenesulfonamide. Each of 'A', 'B', $R_1$, $R_2$, $R_3$, $R_4$, and $R_5$, are as defined earlier.

Compound (2) can be prepared by variety of methods familiar to those skilled in art using a reagent like Boc anhydride from commercially available methane sulfonamide (1). Compound (2) on treatment with diphenylphosphinic chloride under suitable conditions and appropriate solvents provided compound 3 (ref. Synthesis 2003, 15, 2321-24). Compound 3 on treatment with aldehyde or ketone derivative (4) under suitable conditions in presence of base like sodium hydride and appropriate solvent provided compound (5), which can be deprotected under suitable conditions to afford compound (6).

Protection of amine group of 6 with suitable protecting groups like substituted silyl chlorides afforded 7. Compound 7 on treatment with triphenyl phosphine and hexachloroethane followed by ammonia, under suitable conditions and appropriate solvents provide compound of compound 8. Compound 8 on treatment with isocyanato derivative (9) under suitable conditions, base like butyl lithium or sodium hydrate and appropriate solvents yielded compound of formula 10. Compound 10 was subjected to the deprotection with suitable reagent under suitable conditions, followed by reaction with optionally substituted halides provide compounds of formula (I). Chiral separation of the compounds of formula (I) can be achieved using suitable methods like chiral columns via techniques like HPLC; or by using suitable chiral reagents, by a person skilled in the art. Specific reaction conditions, solvents and other parameters necessary for carrying out the process steps as described above are well within the capabilities of a person skilled in the art.

The invention is further illustrated by the following non-limiting examples which describe the preferred way of carrying out the present invention. These are provided without limiting the scope of the present invention in any way.

$^1$H NMR spectral data given in the examples (vide infra) are recorded using a 400 MHz spectrometer (Bruker AVANCE-400) and reported in δ scale. Until and otherwise mentioned the solvent used for NMR is $CDCl_3$ using TMS as the internal standard.

Synthesis of Intermediates

Intermediate-1a: Preparation of tert-butyl (R,E)-2-(2-(N-(tert-butoxycarbonyl)sulfamoyl)vinyl)pyrrolidine-1-carboxylate

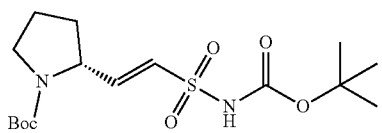 [SMILES: CC(C)(C)OC(=O)NS(=O)(=O)/C=C/[C@H]1CCCN1C(=O)OC(C)(C)C]

A 500 mL, three neck, round-bottomed flask was equipped with magnetic stirrer, thermos-pocket, dry ice bath. tert-butyl ((diphenylphosphoryl)methyl)sulfonylcarbamate (Synthesis 2003, 15, 2321-24) (10 g, 25.3 mmol) was dissolved in DMF (100 mL) under nitrogen atmosphere. It was cooled to −20° C. and added NaH (2.023 g, 50.6 mmol). It was gradually warmed to 25° C. and stirred for 30 min. Again cooled to −20° C. and a solution of (R)-tert-butyl 2-formylpyrrolidine-1-carboxylate (Org. Lett. 2008, 10, 4, 3045-3048) (6.05 g, 30.3 mmol) in DMF (50 mL) was added dropwise over a period of 1 h at −20° C. temp. After the addition reaction mixture was warmed to r.t. and further stirred for 17 h. Reaction mixture was cooled to 0° C. and acidified with saturated citric acid solution (30 mL), and water (200 mL), solid was precipitate out, which was filtered, washed and dried to yield, (R,E)-tert-butyl 2-(2-(N-(tert-butoxycarbonyl)sulfamoyl)vinyl)pyrrolidine-1-carboxylate (4.6 g, 12.22 mmol, 48% yield).

$^1$H NMR (400 MHz, DMSO-$d_6$): δ=11.33 (s, 1H), 6.78-6.67 (m, 1H), 6.52 (d, J=14.2 Hz, 1H), 4.50-4.42 (m, 1H), 3.33-3.27 (m, 2H), 2.1 (br s, 1H), 1.79-1.71 (m, 3H), 1.44-1.35 (m, 18H); MS (ESI): m/z (%)=375.30 (100%) (M−H)$^−$.

Intermediate-1b: Preparation of tert-butyl (S,E)-2-(2-(N-(tert-butoxycarbonyl)sulfamoyl)vinyl)pyrrolidine-1-carboxylate

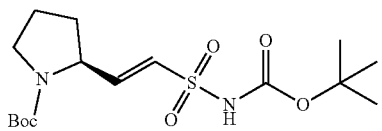 [SMILES: CC(C)(C)OC(=O)NS(=O)(=O)/C=C/[C@@H]1CCCN1C(=O)OC(C)(C)C]

Intermediate-1b was prepared as per the procedure described for synthesis of Intermediate-1a using (S)-tert-butyl 2-formylpyrrolidine-1-carboxylate.

Intermediate-2a: Preparation of tert-butyl (R,E)-2-(2-sulfamoylvinyl)pyrrolidine-1-carboxylate

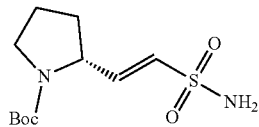

(R,E)-tert-butyl2-(2-(N-(tert-butoxycarbonyl)sulfamyl)vinyl)pyrroldine-1-carboxylate (4 g) was dissolved in DMSO (40 mL) & heated to 85° C. (disappearance of the starting material was monitored by TLC). The reaction was cooled, poured into water (100 mL) & extracted with EtOAc (3×100 mL). The solvent was concentrated in vacuo & purified by column chromatography on silica gel (EtOAc: n-Hexane) to give product.

$^1$H NMR (400 MHz, DMSO-$d_6$) δ=6.99 (s, 2H), 6.40-6.38 (m, 1H), 6.34-6.30 (m, 1H), 4.40-4.32 (m, 2H), 3.28-3.25 (m, 1H), 2.21-1.99 (m, 1H), 1.81-1.67 (m, 3H), 1.38 (m, 9H); MS (ESI): m/z (%)=299.09 (50%) (M+Na)$^+$, 275.09 (100%) (M−1).

Intermediate-2b: Preparation of tert-butyl (S,E)-2-(2-sulfamoylvinyl)pyrrolidine-1-carboxylate

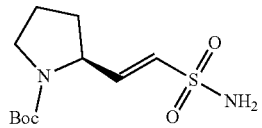 [SMILES: CC(C)(C)OC(=O)N1CCC[C@H]1/C=C/S(N)(=O)=O]

Intermediate-2b was prepared as per the procedure described for synthesis of Intermediate-2a using (S,E)-tert-butyl 2-(2-(N-(tert-butoxycarbonyl)sulfamoyl)vinyl)pyrrolidine-1-carboxylate.

Intermediate-3a: Preparation of tert-butyl (R,E)-2-(2-(N-(tert-butyldiphenylsilyl)sulfamoyl)vinyl)pyrrolidine-1-carboxylate

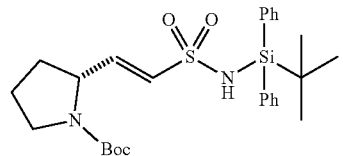 [SMILES: CC(C)(C)OC(=O)N1CCC[C@@H]1/C=C/S(=O)(=O)N[Si](c1ccccc1)(c1ccccc1)C(C)(C)C]

To a stirred solution of tert-butyl (R,E)-2-(2-sulfamoylvinyl)pyrrolidine-1-carboxylate (3.0 g, 10.86 mmol) in THF (30 mL) in 100 mL round bottom flask (equipped with water condenser & anhy. CaCl$_2$ guard tube). TEA (3.78 mL, 27.1 mmol) was added at 0° C. Resulted reaction mixture was stirred at 50° C. for 30 minutes & then TBDPS-Cl (4.18 mL, 16.28 mmol) was added at 50° C. dropwise. After addition reaction mixture was stirred at 50° C. for 17 h. Reaction was monitored by TLC (Reaction mixture+EtOAc+water, TLC was spotted from organic layer). Reaction mixture was diluted with EtOAc (20 mL)+water (20 mL). Organic layer was separated & aq. layer was again extracted with EtOAc (20 mL). All organic layers were mixed together & washed with water (2×30 mL), brine (1×30 mL). Organic layer was dried over Na$_2$SO$_4$ & concentrated in-vaccuo. Crude product was purified by column chromatography, (3.80 g, 7.38 mmol; 68.0% yield)

$^1$H NMR (400 MHz, DMSO-$d_6$): δ=7.80 (bs, 1H), 7.70-7.68 (m, 4H), 7.49-7.42 (m, 6H), 6.18 (d, J=15.2 Hz, 1H), 6.07 (dd, J$_1$=2.4 Hz, J$_2$=14.8 Hz, 1H), 4.33-4.28 (m, 1H), 3.26 (bs, 2H), 2.02-1.97 (m, 1H), 1.67-1.60 (m, 2H), 1.42-1.39 (m, 9H), 0.96 (s, 9H); MS (ESI): m/z (%)=513.15 (100%) (M−1);

Intermediate-3b: Preparation of tert-butyl (S,E)-2-(2-(N-(tert-butyldiphenylsilyl)sulfamoyl)vinyl)pyrrolidine-1-carboxylate

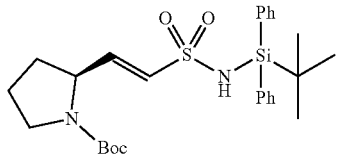 [SMILES: CC(C)(C)OC(=O)N1CCC[C@H]1/C=C/S(=O)(=O)N[Si](c1ccccc1)(c1ccccc1)C(C)(C)C]

Intermediate-3b was prepared as per the procedure described for synthesis of Intermediate-3a using tert-butyl (S,E)-2-(2-sulfamoylvinyl)pyrrolidine-1-carboxylate.

Intermediate-4a: Preparation of tert-butyl (2R)-2-((E)-2-(N-(tert-butyldiphenylsilyl)sulfamidimidoyl)vinyl)pyrrolidine-1-carboxylate

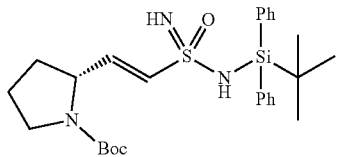 [SMILES: CC(C)(C)OC(=O)N1CCC[C@@H]1/C=C/S(=N)(=O)N[Si](c1ccccc1)(c1ccccc1)C(C)(C)C]

A solution of triphenylphosphine (1.529 g, 5.83 mmol) and perchloroethane (1.380 g, 5.83 mmol) in dry Chloroform (30 mL) was heated to 70° C. for 6 hours under nitrogen gas atmosphere. It was cooled to room temperature and added triethylamine (1.015 mL, 7.29 mmol), stirred for 10 min. and cooled to 0° C. temp. and added a solution of tert-butyl (R,E)-2-(2-(N-(tert-butyldiphenylsilyl)sulfamoyl)vinyl)pyrrolidine-1-carboxylate (2.5 g, 4.86 mmol) in CHCl$_3$ (5 mL). It was stirred for 30 min at 0° C. and ammonia gas was purged at 0° C. temp for 1 hour. The reaction mixture was concentrated under reduced pressure. Crude product was purified by column chromatography. (1.52 g, 2.96 mmol, 61% yield)

$^1$H NMR (400 MHz, DMSO-d$_6$) δ=7.75-7.72 (m, 4H), 7.38-7.35 (m, 6H), 6.58 (s, 2H), 6.38-6.31 (m, 2H), 4.29-4.27 (m, 1H), 3.28-3.18 (m, 2H), 1.99-1.98 (m, 1H), 1.74-1.71 (m, 1H), 1.62-1.55 (m, 2H), 1.41-1.39 (m, 9H), 0.97 (s, 9H); MS (ESI): m/z (%)=514.29 (60%) (M+H)$^+$.

Intermediate-4b: Preparation of tert-butyl (2S)-2-((E)-2-(N-(tert-butyldiphenylsilyl)sulfamidimidoyl)vinyl)pyrrolidine-1-carboxylate

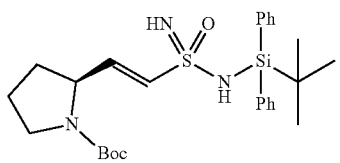 [SMILES: CC(C)(C)OC(=O)N1CCC[C@H]1/C=C/S(=N)(=O)N[Si](c1ccccc1)(c1ccccc1)C(C)(C)C]

Intermediate-4b was prepared as per the procedure described for synthesis of Intermediate-4a using tert-butyl (S,E)-2-(2-(N-(tert-butyldiphenylsilyl)sulfamoyl)vinyl)pyrrolidine-1-carboxylate.

Intermediate-5a: Preparation of tert-butyl (2R)-2-((E)-2-(N'-(tert-butyldiphenylsilyl)-N-((1,2,3,5,6,7-hexahydro-s-indacen-4-yl)carbamoyl)sulfamidimidoyl)vinyl)pyrrolidine-1-carboxylate

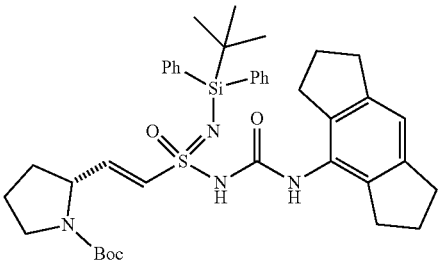 [SMILES: CC(C)(C)OC(=O)N1CCC[C@@H]1/C=C/S(=O)(=N[Si](c1ccccc1)(c1ccccc1)C(C)(C)C)NC(=O)Nc1c2c(cc3c1CCC3)CCC2]

tert-butyl(2R)-2-((E)-2-(N-(tert-butyldiphenylsilyl)sulfamidimidoyl)vinyl)pyrrolidine-1-carboxylate (5.0 g, 9.73 mmol) was dissolved in THF (50 mL) under nitrogen gas atmosphere. It was cooled to −78° C. temp and dropwise added n-butyllithium (4.67 mL, 11.68 mmol) over a period of 10 min. After the addition, reaction mixture was stirred further for 30 min. and then at room temperature for another 30 min. After that a solution of 4-isocyanato-1,2,3,5,6,7-hexahydro-s-indacene (2.327 g, 11.68 mmol) in THF (10 mL) was added in one portion. The resulted suspension was stirred further for 3 hours at room temperature. The reaction mixture was concentrated under reduced pressure and diluted with water (15 mL) and ethyl acetate (20 mL×2), layers were separated, organic layer was washed with water (20 mL), and brine (20 mL) then it was dried over Na$_2$SO$_4$ then conc. under reduced pressure. (7.59 g, 10.64 mmol) $^1$H NMR (400 MHz, DMSO-d$_6$) δ=9.8 (bs, 1H), 7.95 (bs, 1H), 7.78-7.77 (m, 4H), 7.34-7.30 (m, 6H), 6.87 (s, 1H), 6.63 (d, J=7.2 Hz, 1H), 6.37-6.34 (m, 1H), 4.40 (bs, 1H), 3.25-3.17 (m, 2H), 2.77 (t, J=7.2 Hz, 4H), 2.69-2.50 (m, 4H), 1.99-1.89 (m, 5H), 1.72-1.60 (m, 3H), 1.41-1.39 (m, 9H), 0.97 (s, 9H); MS (ESI): m/z (%)=713.51 (100%) (M)$^+$.

Intermediate-5b: Preparation of tert-butyl (2S)-2-((E)-2-(N'-(tert-butyldiphenylsilyl)-N-((1,2,3,5,6,7-hexahydro-s-indacen-4-yl)carbamoyl)sulfamidimidoyl)vinyl)pyrrolidine-1-carboxylate

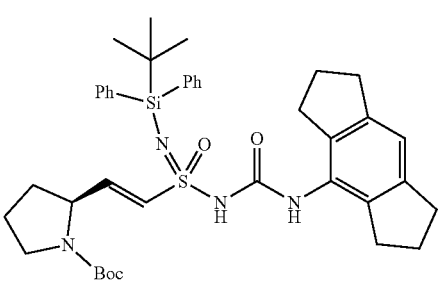 [SMILES: CC(C)(C)OC(=O)N1CCC[C@H]1/C=C/S(=O)(=N[Si](c1ccccc1)(c1ccccc1)C(C)(C)C)NC(=O)Nc1c2c(cc3c1CCC3)CCC2]

Intermediate-5b was prepared as per the procedure described for synthesis of Intermediate-5a using tert-butyl(2S)-2-((E)-2-(N-(tert-butyldiphenylsilyl)sulfamidimidoyl)vinyl)pyrrolidine-1-carboxylate.

Intermediate-6a: Preparation of tert-butyl (S,E)-2-(2-(N-(tert-butyldiphenylsilyl)sulfamoyl)vinyl)-2-methylpyrrolidine-1-carboxylate

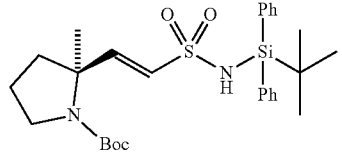 [SMILES: CC(C)(C)OC(=O)N1CCC[C@@]1(C)/C=C/S(=O)(=O)N[Si](c1ccccc1)(c1ccccc1)C(C)(C)C]

To a solution of tert-butyl (S,E)-2-methyl-2-(2-sulfamoylvinyl)pyrrolidine-1-carboxylate (CAS: 2455521-72-7) (6.6 g, 22.73 mmol) in THF (38 mL) under nitrogen gas atmosphere, TEA (7.92 mL, 56.8 mmol) was added at 0° C. Then the reaction mixture was stirred for 30 min. at 50° C. Then TBDPS-Cl (7.30 mL, 28.4 mmol) was added dropwise at 50° C. After addition reaction mixture was stirred at 50° C. for 17 h. TLC shows starting material so added TEA (7.92 mL, 56.8 mmol) and TBDPS-Cl (7.30 mL, 28.4 mmol) two times over a interval of 8 h. Completion of reaction checked by TLC. The reaction was concentrated in vacuo. Crude product was purified by column chromatography, (ethyl acetate: n-hexane) (gradient) to yield, tert-butyl (S,E)-2-(2-(N-(tert-butyldiphenylsilyl)sulfamoyl)vinyl)2-methylpyrrolidine-1-carboxylate (8.5 g, 16.07 mmol, 71% yield).

1H NMR (400 MHz, DMSO-d6): δ=7.79 (bs, 1H), 7.71-7.69 (m, 4H), 7.49-7.38 (m, 6H), 6.36-6.21 (m, 1H), 6.06-5.98 (m, 1H), 1.80-1.72 (m, 3H), 1.60-1.60 (m, 1H), 1.53-1.48 (m, 1H), 1.43-1.37 (m, 6H), 1.33-1.29 (m, 6H), 0.97 (s, 9H), 0.88-0.81 (m, 1H); ESI-Q-TOF-MS: m/z [M–H]+ calcd for [C28H39N2O4SSi]+: 527.2400; found: 527.2740

Intermediate-6b: Preparation of tert-butyl (R,E)-2-(2-(N-(tert-butyldiphenylsilyl)sulfamoyl)vinyl)-2-methylpyrrolidine-1-carboxylate

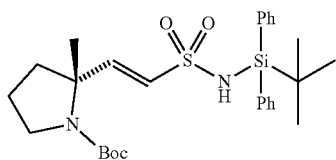

Intermediate-6b was prepared as per the procedure described for synthesis of Intermediate-6a using tert-butyl (R,E)-2-methyl-2-(2-sulfamoylvinyl)pyrrolidine-1-carboxylate.

Intermediate-7a: Preparation of tert-butyl (2S)-2-((E)-2-(N-(tert-butyldiphenylsilyl)sulfamidimidoyl)vinyl)-2-methylpyrrolidine-1-carboxylate

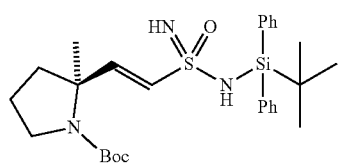 [SMILES: CC(C)(C)OC(=O)N1CCC[C@@]1(C)/C=C/S(=N)(=O)N[Si](c1ccccc1)(c1ccccc1)C(C)(C)C]

A solution of triphenylphosphine (5.48 g, 20.90 mmol) and perchloroethane (4.95 g, 20.90 mmol) in dry CHCl3 (55 mL) was heated at 70° C. for 6 h under nitrogen gas atmosphere. Solid was precipitated out, it was cooled to RT and added TEA (3.97 mL, 28.5 mmol) and reaction mixture was stirred for 10 min. Then it was cooled to 0° C. temp. and added a solution of tert-butyl (2S)-2-((E)-2-(N-(tert-butyldiphenylsilyl)sulfamidimidoyl)vinyl)-2-m thylpyrrolidine-1-carboxylate in CHCl3 (45 mL), in one lot Then the reaction mixture was stirred for 60 min at 0° C. and ammonia gas was purged at 0° C. temp for 1 h. Completion of reaction checked by TLC. The reaction was concentrated in vacuo and crude product was purified by column chromatography, (ethyl acetate: n-hexane) (gradient) to yield, tert-butyl (2S)-2-((E)-2-(N-(tert-butyl diphenyl silyl)sulfamidimidoyl)vinyl)-2-methylpyrrolidine-1-carboxylate (7.6 g, 14.40 mmol, 90% yield)

1H NMR (400 MHz, DMSO-d6) δ=7.76-7.73 (m, 4H), 7.35-7.34 (m, 6H), 6.55 (s, 2H), 6.46-6.24 (m, 2H), 3.33-3.26 (m, 2H), 1.78-1.63 (m, 3H), 1.41-1.37 (m, 6H), 1.33-1.24 (m, 6H), 0.98 (s, 9H); ESI-Q-TOF-MS: m/z [M–H]− calcd for [C28H42N3O3SSi]+: 528.2716; found: 528.3496

Intermediate-7b: Preparation of tert-butyl (2R)-2-((E)-2-(N-(tert-butyldiphenylsilyl)sulfamidimidoyl)vinyl)-2-methylpyrrolidine-1-carboxylate

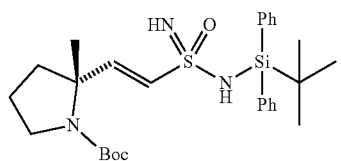

Intermediate-7b was prepared as per the procedure described for synthesis of Intermediate-7a using tert-butyl (2R)-2-((E)-2-(N-(tert-butyldiphenylsilyl)sulfamidimidoyl)vinyl)-2-methylpyrrolidine-1-carboxylate

Intermediate-8a: Preparation of tert-butyl (2S)-2-((E)-2-(N'-(tert-butyldiphenylsilyl)-N-((1,2,3,5,6,7-hexahydro-s-indacen-4-yl)carbamoyl)sulfamidimidoyl)vinyl)-2-methylpyrrolidine-1-carboxylate

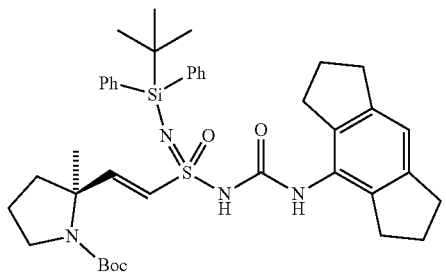 [SMILES: CC(C)(C)OC(=O)N1CCC[C@@]1(C)/C=C/S(=O)(=N[Si](c1ccccc1)(c1ccccc1)C(C)(C)C)NC(=O)Nc1c2c(cc3c1CCC3)CCC2]

A solution of tert-butyl (2S)-2-((E)-2-(N-(tert-butyldiphenylsilyl)sulfamidimidoyl)vinyl)-2-methylpyrrolidine-1-carboxylate (8.5 g, 16.10 mmol) in THF (32 mL) under nitrogen gas atmosphere was cooled to −78° C. temp and drop-wise added n-butyllithium (9.66 mL, 24.16 mmol) over a period of 10 min. After the addition reaction mixture was stirred further for 30 min. then at room temperature for another 30 min. There after a solution of 4-isocyanato-1,2,3,5,6,7-hexahydro-s-indacene (3.85 g, 19.33 mmol) in THF (3 mL) was added in one portion. The resulted suspension was stirred further for 3 h at RT. Completion of reaction checked by TLC. The reaction diluted water (50 mL) and ethyl acetate (50 mL), the aqueous layer was back extracted with ethyl acetate (2×50 mL), the combined organic layer was dried over $Na_2SO_4$ (sodium sulfate). The solvent was evaporated to yield, tert-butyl (2S)-2-((E)-2-(N'-(tert-butyldiphenylsilyl)-N-((1,2,3,5,6,7-hexahydro-s-indacen-4-yl)carbamoyl)sulfamidimidoyl)vinyl)-2-methylpyrrolidine-1-carboxylate (11.70 g, 16.09 mmol, 100% yield).

$^1$H NMR (400 MHz, DMSO-$d_6$) δ=7.79-7.78 (m, 4H), 7.32-7.19 (m, 6H), 6.88-6.65 (m, 2H), 3.33-3.27 (m, 2H), 2.77-2.71 (m, 4H), 2.69-2.66 (m, 4H), 1.99-1.90 (m, 5H), 1.76-1.71 (m, 4H), 1.43-1.33 (m, 12H), 0.97 (s, 9H); ESI-Q-TOF-MS: m/z [M+H]$^+$ calcd for [C41H55N4O4SSi]$^+$: 727.3713; found: 727.3699

Intermediate-8b: Preparation of tert-butyl (2R)-2-((E)-2-(N'-(tert-butyldiphenylsilyl)-N-((1,2,3,5,6,7-hexahydro-s-indacen-4-yl)carbamoyl)sulfamidimidoyl)vinyl)-2-methylpyrrolidine-1-carboxylate

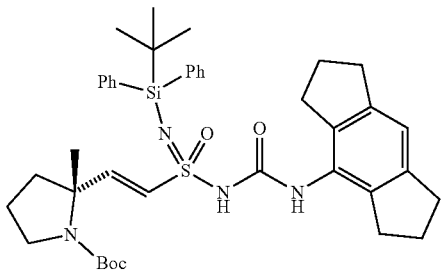

Intermediate-8b was prepared as per the procedure described for synthesis of Intermediate-8a using tert-butyl (2R)-2-((E)-2-(N-(tert-butyldiphenylsilyl)sulfamidimidoyl)vinyl)-2-methylpyrrolidine-1-carboxylate Intermediate-9a: Preparation of (E)-N'-(tert-butyldiphenylsilyl)-N-((1,2,3,5,6,7-hexahydro-s-indacen-4-yl)carbamoyl)-2-((S)-2-methylpyrrolidin-2-yl)ethene-1-sulfonimidamide HCl

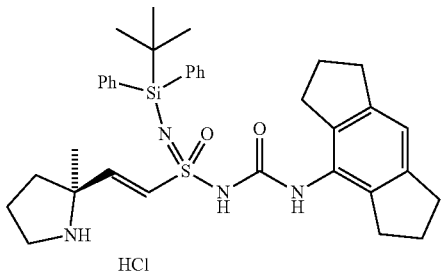 [SMILES: CC(C)(C)[Si](N=S(=O)(/C=C/[C@]1(C)CCCN1)NC(=O)Nc1c2c(cc3c1CCC3)CCC2)(c1ccccc1)c1ccccc1 ; Cl]

To tert-butyl (2S)-2-((E)-2-(N'-(tert-butyldiphenylsilyl)-N-((1,2,3,5,6,7-hexahydro-s-indacen-4-yl)carbamoyl)sulfamidimidoyl)vinyl)-2-methylpyrrolidine-1-carboxylate (0.5 g, 0.688 mmol) was added EtOAc: HCl (5 mL, 165 mmol) solution at 0° C. The reaction was stirred for 2 h. TLC was checked, no SM was observed. The reaction mixture was concentrated in vacuo to give crude product. The residue was solidified by triturating from DIPE (25 mL) & washed with DIPE (10 mL×3), dried on vacuo to give product. (E)-N'-(tert-butyldiphenylsilyl)-N-((1,2,3,5,6,7-hexahydro-s-indacen-4-yl)carbamoyl)-2-((S)-2-methylpyrrolidin-2-yl)ethene-1-sulfonimidamide hydrochloride. MS (ESI): m/z (%)=626.9 (20%) (M−TFA)$^-$;

Intermediate-9b: Preparation of (E)-N'-(tert-butyldiphenylsilyl)-N-((1,2,3,5,6,7-hexahydro-s-indacen-4-yl)carbamoyl)-2-((R)-2-methylpyrrolidin-2-yl)ethene-1-sulfonimidamide HCl

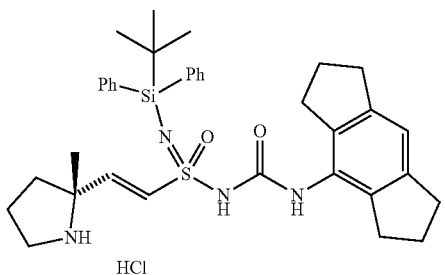

Intermediate-9b was prepared as per the procedure described for synthesis of Intermediate-9a using tert-butyl (2R)-2-((E)-2-(N'-(tert-butyldiphenylsilyl)-N-((1,2,3,5,6,7-hexahydro-s-indacen-4-yl)carbamoyl)sulfamidimidoyl)vinyl)-2-methylpyrrolidine-1-carboxylate Example-1: tert-butyl (2R)-2-((E)-2-(N-((1,2,3,5,6,7-hexahydro-s-indacen-4-yl)carbamoyl)sulfamidimidoyl)vinyl)pyrrolidine-1-carboxylate

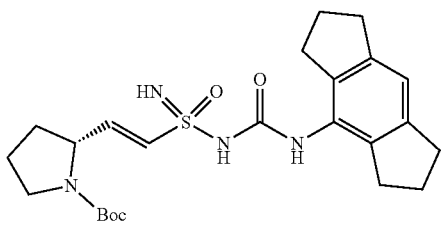 [SMILES: CC(C)(C)OC(=O)N1CCC[C@@H]1/C=C/S(=N)(=O)NC(=O)Nc1c2c(cc3c1CCC3)CCC2]

tert-butyl(2R)-2-((E)-2-(N'-(tert-butyldiphenylsilyl)-N-((1,2,3,5,6,7-hexahydro-s-indacen-4-yl)carbamoyl)sulfamidimidoyl)vinyl)pyrrolidine-1-carboxylate (2.8 g, 3.93 mmol) was dissolved in THF (28 mL) under nitrogen gas atmosphere. It was cooled to 0° C. temp. and dropwise added TBAF (4.71 mL, 4.71 mmol) over a period of 10 min. After the addition, reaction mixture was stirred further for 48 min. at room temperature. The reaction mixture was concentrated under reduced pressure and purified by column chromatography. (1.~01 g, 2.091 mmol, 53.3% yield)

$^1$H NMR (400 MHz, DMSO-$d_6$): δ=8.30 (s, 1H), 7.20 (s, 2H), 6.87 (s, 1H), 6.64 (dd, $J_1$=5.6 Hz, $J_2$=14.8 Hz, 1H), 6.54-6.51 (m, 1H), 4.47 (br s, 1H), 3.29 (d, J=6.4 Hz, 2H), 2.78 (t, J=7.6 Hz, 4H), 2.70 (t, J=6.8 Hz, 4H), 2.09-2.06 (m, 1H), 1.93 (quin, J=7.2 Hz, 4H), 1.80-1.71 (m, 3H), 1.36 (s, 9H); MS (ESI): m/z (%)=475.22 (100%) (M+H)$^+$.

Example-2: tert-butyl (2S)-2-((E)-2-(N-((1,2,3,5,6,7-hexahydro-s-indacen-4-yl)carbamoyl)sulfamidimidoyl)vinyl)-2-methylpyrrolidine-1-carboxylate

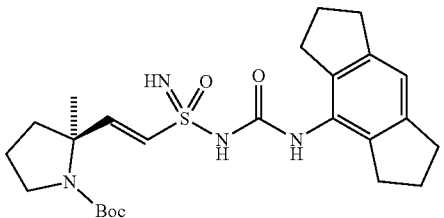 [SMILES: CC(C)(C)OC(=O)N1CCC[C@@]1(C)/C=C/S(=N)(=O)NC(=O)Nc1c2c(cc3c1CCC3)CCC2]

tert-butyl (2S)-2-((E)-2-(N'-(tert-butyldiphenylsilyl)-N-((1,2,3,5,6,7-hexahydro-s-indacen-4-yl)carbamoyl)sulfamidimidoyl)vinyl)-2-methylpyrrolidine-1-carboxylate (0.4 g, 0.550 mmol) was dissolved in a mixture of Acetonitrile (19 mL) and Water (1 mL) under nitrogen gas atmosphere. It was cooled to 0° C. temp. and dropwise added DBU (0.083 mL, 0.550 mmol) over a period of 5 min. after the addition RM was stirred further for 17 h. at RT. Completion of reaction checked by TLC. The R.M was concentrated under reduced pressure and purified by column chromatography. (ethyl acetate:n-hexane) (gradient) to yield, tert-butyl (2S)-2-((E)-2-(N-((1,2,3,5,6,7-hexahydro-s-indacen-4-yl)carbamyl)sulfamidimidoyl)vinyl)-2-methylpyrrolidine-1-carboxylate (0.14 g, 0.282 mmol, 51.2% yield).

$^1$H NMR (400 MHz, DMSO-d$_6$): δ=8.3 (br s, 1H), 7.2 (s, 2H), 6.87 (s, 1H), 6.70-6.55 (m, 2H), 3.37 (br s, 2H), 2.78 (t, J=7.2 Hz, 4H), 2.70 (t, J=7.2 Hz, 4H), 1.94 (t, J=7.2 Hz, 5H), 1.81-1.75 (m, 3H), 1.51-1.47 (m, 3H), 1.40-1.36 (m, 9H); ESI-Q-TOF-MS: m/z [M+H]$^+$ calcd for [C25H37N4O4S]$^+$: 489.2536; found: 489.2338

Example-3: tert-butyl (2S)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxylate

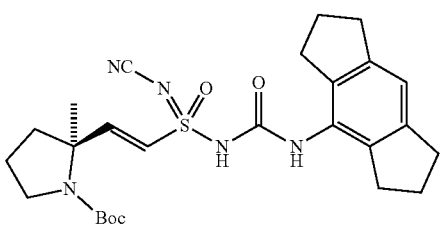 [SMILES: CC(C)(C)OC(=O)N1CCC[C@@]1(C)/C=C/S(=O)(=NC#N)NC(=O)Nc1c2c(cc3c1CCC3)CCC2]

tert-butyl (2S)-2-((E)-2-(N-((1,2,3,5,6,7-hexahydro-s-indacen-4-yl)carbamoyl)sulfamidimidoyl)vinyl)-2-methylpyrrolidine-1-carboxylate (0.64 g, 1.310 mmol) was taken in DMF (5 mL) under nitrogen gas atmosphere. TEA (0.730 mL, 5.24 mmol) and cyanic bromide (0.277 g, 2.62 mmol) was added and the RM was stirred further for 17 h at RT. TLC was checked no starting material observed. The R.M was filtered, washed with ethyl acetate and concentrated under reduced pressure to crude was purified by column chromatography, (Methanol: Dichloromethane) (Gradient), to yield, tert-butyl (2S)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxylate (0.564 g, 1.073 mmol, 82% yield).

$^1$H NMR (400 MHz, DMSO-d$_6$) δ=8.92 (s, 1H), 7.84 (s, 1H), 6.82 (s, 1H), 6.50-6.45 (m, 2H), 3.37-3.35 (m, 2H), 2.77 (t, J=7.2 Hz, 4H), 2.70 (t, J=7.2 Hz, 4H), 1.92 (t, J=7.2 Hz, 6H), 1.74 (br s, 2H), 1.49-1.45 (m, 3H), 1.39-1.37 (m, 9H); ESI-Q-TOF-MS: m/z [M+H]$^+$ calcd for [C26H36N5O4S]$^+$: 514.2488; found: 514.3010

Example-4: (E)-N'-cyano-N-((1,2,3,5,6,7-hexahydro-s-indacen-4-yl)carbamoyl)-2-((S)-2-methylpyrrolidin-2-yl)ethene-1-sulfonimidamide hydrochloride

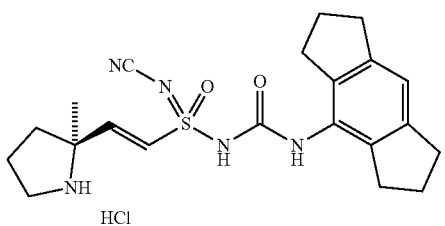 [SMILES: C[C@@]1(/C=C/S(=O)(=NC#N)NC(=O)Nc2c3c(cc4c2CCC4)CCC3)CCCN1 ; Cl]

tert-butyl (2S)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxylate (0.5 g, 0.973 mmol) was dissolved in Dioxane:HCl solution (5 mL) and RM was stirred further for 2 h. TLC was checked no starting material observed. The R.M was diluted with DIPE solid ppt, filtered it and washed with DIPE, to yield, (E)-N'-cyano-N-((1,2,3,5,6,7-hexahydro-s-indacen-4-yl)carbamoyl)-2-((S)-2-methylpyrrolidin-2-yl)ethene-1-sulfonimidamide hydrochloride (0.472 g, 0.997 mmol).

$^1$H NMR (400 MHz, DMSO-d$_6$) δ=10.10 (s, 1H), 9.79-9.4 (m, 1H), 7.15-7.09 (m, 1H), 6.91-6.77 (m, 2H), 3.39-3.16 (m, 2H), 2.79 (t, J=7.2 Hz, 4H), 2.71 (t, J=6.8 Hz, 4H), 2.12-1.91 (m, 8H), 1.51-1.46 (m, 3H); ESI-Q-TOF-MS: m/z [M−HCl+H]$^+$ calcd for [C21H28N5O2S]$^+$: 414.1964; found: 414.2505

Example-5: (E)-2-((S)-1,2-dimethylpyrrolidin-2-yl)-N-((1,2,3,5,6,7-hexahydro-s-indacen-4-yl)carbamoyl)ethene-1-sulfonimidamide

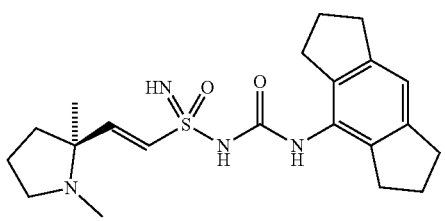 [SMILES: CN1CCC[C@@]1(C)/C=C/S(=N)(=O)NC(=O)Nc1c2c(cc3c1CCC3)CCC2]

To a solution of (E)-N'-(tert-butyldiphenylsilyl)-N-((1,2,3,5,6,7-hexahydro-s-indacen-4-yl)carbamoyl)-2-((S)-2-methylpyrrolidin-2-yl)ethene-1-sulfonimidamide hydrochloride (0.5 g, 0.754 mmol) in MeOH (10 mL) under nitrogen gas atmosphere. TEA (0.197 mL, 1.412 mmol) was added and RM was stirred for 10 min. at RT. then a paraformaldehyde (0.071 g, 2.353 mmol) was added and RM was stirred for 10 min. at RT. Then the RM was cooed to 0° C. temp. and portion wise added sodium cyanoborohydride (0.089 g, 1.412 mmol). After the addition RM was warmed to RT and stirred for 17 h. TLC was checked no starting material was observed. The reaction was concentrated at 35° C. under reduced pressure and crude was purified by column chromatography using (MeOH: DCM) (Gradient) to yield Example 5 and Example 6.

¹H NMR (400 MHz, DMSO-d₆) δ=8.31 (s, 1H), 7.17 (s, 2H), 6.87 (s, 1H), 6.81-6.70 (m, 1H), 6.58-6.54 (m, 1H), 2.78 (t, J=7.2 Hz, 5H), 2.70 (t, J=7.2 Hz, 5H), 2.18 (br s, 3H), 1.93 (t, J=7.2 Hz, 5H), 1.78 (br s, 3H), 1.24-1.12 (m, 3H); MS (TOF): m/z (%)=403.2044 (100%) (M+H)⁺

Example-6: (E)-2-((S)-1,2-dimethylpyrrolidin-2-yl)-N-((1,2,3,5,6,7-hexahydro-s-indacen-4-yl)carbamoyl)-N'-methylethene-1-sulfonimidamide

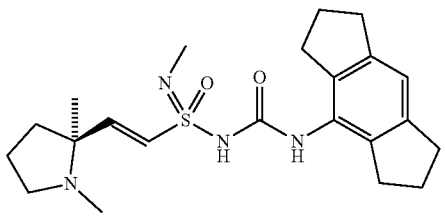 [SMILES: CN=S(=O)(/C=C/[C@]1(C)CCCN1C)NC(=O)Nc1c2c(cc3c1CCC3)CCC2]

¹H NMR (400 MHz, DMSO-d₆) δ=8.40 (br s, 1H), 7.00 (s, 1H), 6.88 (s, 1H), 6.56 (d, J=15.2 Hz, 1H), 6.45 (dd, J₁=6.4 Hz, J₂=15.6 Hz, 1H), 2.79 (t, J=7.2 Hz, 5H), 2.70 (t, J=6.8 Hz, 6H), 2.14 (s, 3H), 1.94 (quin, J=7.2 Hz, 6H), 1.77-1.72 (m, 4H), 1.24-1.10 (m, 3H); MS (TOF): m/z (%)=417.2207 (100%) (M+H)⁺;

Example-7: (E)-N'-cyano-2-((S)-1,2-dimethylpyrrolidin-2-yl)-N-((1,2,3,5,6,7-hexahydro-s-indacen-4-yl)carbamoyl)ethene-1-sulfonimidamide

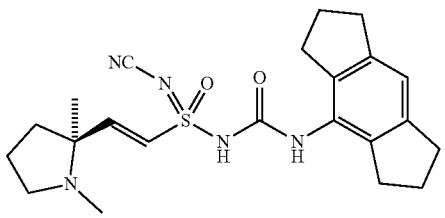 [SMILES: CN1CCC[C@@]1(C)/C=C/S(=O)(=NC#N)NC(=O)Nc1c2c(cc3c1CCC3)CCC2]

(E)-2-((S)-1,2-dimethylpyrrolidin-2-yl)-N-((1,2,3,5,6,7-hexahydro-s-indacen-4-yl)carbamoyl)ethene-1-sulfonimidamide (0.090 g, 0.224 mmol) was taken in DMF (5 mL) under nitrogen gas atmosphere. TEA (0.125 mL, 0.894 mmol) and cyanic bromide (BrCN) (0.047 g, 0.447 mmol) was added and the RM was stirred further for 17 h at RT. TLC was checked no starting material observed. The R.M was filtered, washed with EA and concentrated under vacuo. Crude was purified by preparative HPLC, (E)-N'-cyano-2-((S)-1,2-dimethylpyrrolidin-2-yl)-N-((1,2,3,5,6,7-hexahydro-s-indacen-4-yl)carbamoyl)ethene-1-sulfonimidamide.

¹H NMR (400 MHz, DMSO-d₆) δ=9.94 (s, 1H), 8.06 (s, 1H), 6.97 (d, J=16.0 Hz, 1H), 6.83 (s, 1H), 6.56-6.48 (m, 1H), 3.58 (br s, 1H), 3.24-3.12 (m, 1H), 2.77 (t, J=7.2 Hz, 4H), 2.69 (t, J=7.2 Hz, 7H), 2.10-1.99 (m, 3H), 1.95-1.88 (m, 5H), 1.53-1.36 (m, 3H); ESI-Q-TOF-MS: m/z [M−HCl+H]⁺ calcd for [C22H30N5O2S]⁺: 428.2120; found: 428.2052

Alternatively Example 7 Can Also be Prepared As

To a solution of (E)-N'-cyano-N-((1,2,3,5,6,7-hexahydro-s-indacen-4-yl)carbamoyl)-2-((S)-2-methylpyrrolidin-2-yl)ethene-1-sulfonimidamide hydrochloride (0.235 g, 0.522 mmol) in MeOH (9 mL), TEA (0.087 mL, 0.627 mmol) was added under nitrogen gas atmosphere and reaction mixture was stirred for 10 min. at room temperature. then paraformaldehyde (0.031 g, 1.044 mmol) was added and reaction mixture was stirred for 10 min. at room temperature. Then the reaction mixture was cooed to 0° C. temp. and portionwise added sodium cyanoborohydride (0.039 g, 0.627 mmol). After the addition reaction mixture was warmed to room temperature and stirred for 17 h. TLC was checked no starting material was observed. The reaction was concentrated at 35° C. under reduced pressure and crude product was purified by preparative HPLC. To obtained (E)-N'-cyano-2-((S)-1,2-dimethylpyrrolidin-2-yl)-N-((1,2,3,5,6,7-hexahydro-s-indacen-4-yl)carbamoyl)ethene-1-sulfonimidamide.

¹H NMR (400 MHz, DMSO-d₆) δ=9.94 (s, 1H), 8.06 (s, 1H), 6.97 (d, J=16.0 Hz, 1H), 6.83 (s, 1H), 6.56-6.48 (m, 1H), 3.58 (br s, 1H), 3.24-3.12 (m, 1H), 2.77 (t, J=7.2 Hz, 4H), 2.69 (t, J=7.2 Hz, 7H), 2.10-1.99 (m, 3H), 1.95-1.88 (m, 5H), 1.53-1.36 (m, 3H); ESI-Q-TOF-MS: m/z [M−HCl+H]⁺ calcd for [C22H30N5O2S]⁺: 428.2120; found: 428.2052.

Using appropriate starting materials and suitable modifications of the process described in example 1-7, including suitable addition and/or deletion of steps as may be necessary which are well within the scope of a person skilled in the art, e.g. deprotection with suitable reagent under suitable conditions, followed by reaction with optionally substituted halides, the following compounds were prepared in an analogues manner.

Example-8: (E)-N'-cyano-2-((R)-1-(cyclohexylsulfonyl)pyrrolidin-2-yl)-N-((1,2,3,5,6,7-hexahydro-s-indacen-4-yl)carbamoyl)ethene-1-sulfonimidamide

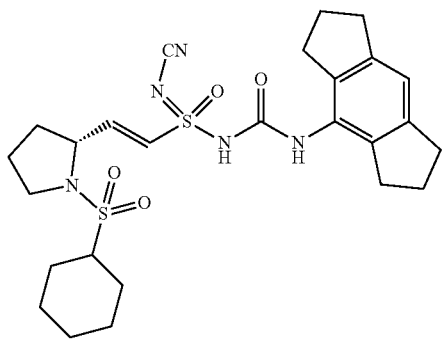 [SMILES: N#CN=S(=O)(/C=C/[C@H]1CCCN1S(=O)(=O)C1CCCCC1)NC(=O)Nc1c2c(cc3c1CCC3)CCC2]

¹H NMR (400 MHz, DMSO-d₆) δ=7.88 (s, 1H), 7.21-6.96 (m, 1H), 6.81 (s, 1H), 6.71 (dd, J₁=1.2 Hz, J₂=15.2 Hz, 1H), 6.40-6.33 (m, 1H), 4.51 (bs, 1H), 3.48-3.42 (m, 1H), 3.29-3.24 (m, 1H), 3.15-3.03 (m, 1H), 2.78 (t, J=7.2 Hz, 4H), 2.71 (t, J=7.6 Hz, 4H), 2.17-2.05 (m, 1H), 1.97-1.85 (m, 8H), 1.77-1.67 (m, 3H), 1.51-1.49 (m, 1H), 1.39-1.30 (m, 3H), 1.26-1.18 (m, 1H), 1.17-1.05 (m, 1H); MS (ESI): m/z (%)=546.24 (100%) (M+H)⁺.

Example-9: (E)-N'-cyano-2-((R)-14(2-cyanophenyl)sulfonyl)pyrrolidin-2-yl)-N-((1,2,3,5,6,7-hexahydro-s-indacen-4-yl)carbamoyl)ethene-1-sulfonimidamide

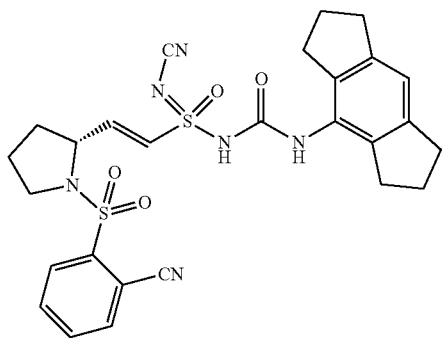 [SMILES: N#CN=S(=O)(/C=C/[C@H]1CCCN1S(=O)(=O)c1ccccc1C#N)NC(=O)Nc1c2c(cc3c1CCC3)CCC2]

¹H NMR (400 MHz, DMSO-d₆) δ=8.11-8.08 (m, 2H), 7.94-7.83 (m, 3H), 7.21-6.95 (m, 1H), 6.82 (s, 1H), 6.72 (dd, J₁=1.2 Hz, J₂=15.2 Hz, 1H), 6.33-6.27 (m, 1H), 4.58 (b s, 1H), 3.46-3.43 (m, 2H), 2.77 (t, J=7.2 Hz, 4H), 2.71 (t, J=6.8 Hz, 4H), 1.95-1.83 (m, 6H), 1.75-1.73 (m, 2H); MS (ESI): m/z (%)=565.19 (100%) (M+H)⁺.

Example—10: (E)-N'-cyano-N-((1,2,3,5,6,7-hexahydro-s-indacen-4-yl)carbamoyl)-2-((R)-pyrrolidin-2-yl)ethene-1-sulfonimidamide hydrochloride

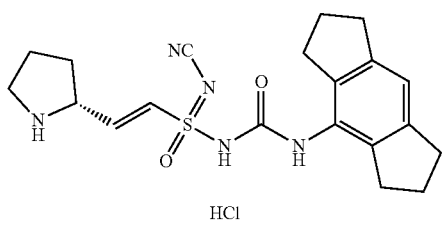 [SMILES: N#CN=S(=O)(/C=C/[C@H]1CCCN1)NC(=O)Nc1c2c(cc3c1CCC3)CCC2 ; Cl]

¹H NMR (400 MHz, DMSO-d₆) δ=9.54 (s, 1H), 9.10 (s, 1H)), 7.15 (d, J=15.2 Hz, 1H), 6.88 (s, 1H), 6.81-6.74 (m, 1H), 4.28 (br s, 1H), 3.26-3.20 (m, 2H), 2.78 (t, J=7.2 Hz, 4H), 2.71 (t, J=6.8 Hz, 4H), 2.20-2.14 (m, 1H), 2.01-1.87 (m, 6H), 1.79-1.72 (m, 1H); MS (ESI): m/z (%)=400.20 (100%) (M+H)⁺, 398.15 (100%) (M-1)⁻.

Example—11: (E)-N'-cyano-N-((1,2,3,5,6,7-hexahydro-s-indacen-4-yl)carbamoyl)-2-((R)-1-methylpyrrolidin-2-yl)ethene-1-sulfonimidamide

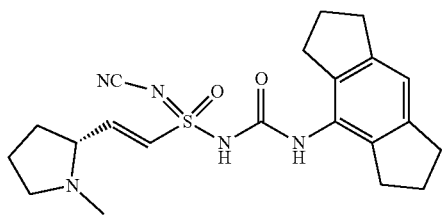 [SMILES: CN1CCC[C@@H]1/C=C/S(=O)(=NC#N)NC(=O)Nc1c2c(cc3c1CCC3)CCC2]

¹H NMR (400 MHz, DMSO-d₆) δ=9.82 (s, 1H), 8.06 (s, 1H), 7.11-7.02 (m, 1H), 6.83 (s, 1H), 6.43-6.35 (m, 1H), 4.99 (br s, 1H), 3.62-3.61 (m, 1H), 3.09-3.07 (m, 1H), 2.77 (t, J=7.2 Hz, 7H), 2.70 (t, J=7.2 Hz, 4H), 2.33-2.27 (m, 1H), 2. 1-1.88 (m, 7H); MS (TOF): m/z (%)=414.1897 (100%) (M+H)⁺, 412.1765 (100%) (M-1)⁻.

Example—12: tert-butyl (2R)-2-((E)-2-(N-((1,2,3,5,6,7-hexahydro-s-indacen-4-yl)carbamoyl)sulfamidimidoyl)vinyl)-2-methylpyrrolidine-1-carboxylate

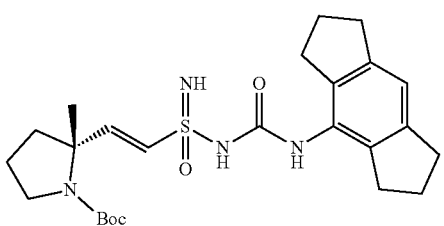 [SMILES: CC(C)(C)OC(=O)N1CCC[C@]1(C)/C=C/S(=N)(=O)NC(=O)Nc1c2c(cc3c1CCC3)CCC2]

¹H NMR (400 MHz, DMSO-d₆) δ=8.31 (br s, 1H), 7.2 (s, 2H), 6.88 (s, 1H), 6.70-6.51 (m, 2H), 3.43 (br s, 2H), 2.79 (t, J=7.2 Hz, 4H), 2.71 (t, J=7.2 Hz, 4H), 1.96 (t, J=7.2 Hz, 5H), 1.84-1.70 (m, 3H), 1.51-1.47 (m, 3H), 1.40-1.36 (m, 9H); MS (TOF): m/z (%)=489.3021 (100%) (M+H)⁺, 487.2582 (100%) (M-1)⁻;

Example—13: tert-butyl (2R)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxylate

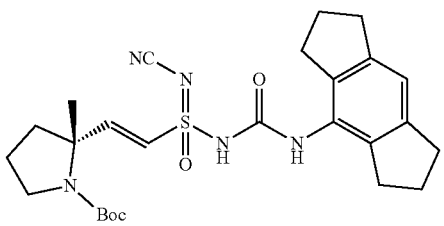 [SMILES: CC(C)(C)OC(=O)N1CCC[C@]1(C)/C=C/S(=O)(=NC#N)NC(=O)Nc1c2c(cc3c1CCC3)CCC2]

¹H NMR (400 MHz, DMSO-d₆) δ=8.97 (s, 1H), 7.83 (s, 1H), 6.81 (s, 1H), 6.49-6.44 (m, 2H), 3.37-3.35 (m, 2H), 2.76 (t, J=6.8 Hz, 4H), 2.70 (t, J=7.2 Hz, 4H), 1.91 (t, J=7.2 Hz, 6H), 1.72 (br s, 2H), 1.48-1.44 (m, 3H), 1.38-1.36 (m, 9H); MS (TOF): m/z (%)=514.2476 (40%) (M+H)⁺, 512.2289 (100%) (M-1)⁻.

Example—14: (E)-N'-cyano-N-((1,2,3,5,6,7-hexahydro-s-indacen-4-yl)carbamoyl)-2-((R)-2-methylpyrrolidin-2-yl)ethene-1-sulfonimidamide hydrochloride

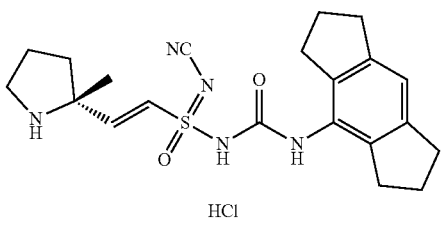 [SMILES: C[C@]1(/C=C/S(=O)(=NC#N)NC(=O)Nc2c3c(cc4c2CCC4)CCC3)CCCN1 ; Cl]

¹H NMR (400 MHz, DMSO-d₆) δ=9.99 (s, 1H), 9.53-9.25 (m, 1H), 7.12-7.07 (m, 1H), 6.91-6.82 (m, 2H), 5.32 (br s, 2H), 3.31-3.23 (m, 2H), 2.79 (t, J=7.2 Hz, 4H), 2.71 (t, J=7.2 Hz, 4H), 2.11-2.07 (m, 1H), 2.02-1.87 (m, 7H); 1.52 (br s, 3H); MS (TOF): m/z (%)=414.1941 (100%) (M−HCl+H)⁺, 412.1773 (100%) (M−HCl−1)⁻.

Example—15: (E)-N'-cyano-2-((R)-1,2-dimethylpyrrolidin-2-yl)-N-((1,2,3,5,6,7-hexahydro-s-indacen-4-yl)carbamoyl)ethene-1-sulfonimidamide

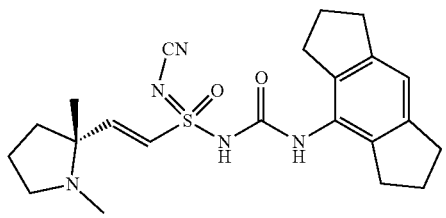 [SMILES: CN1CCC[C@]1(C)/C=C/S(=O)(=NC#N)NC(=O)Nc1c2c(cc3c1CCC3)CCC2]

¹H NMR (400 MHz, DMSO-d₆): δ=9.98 (s, 1H), 8.03 (s, 1H), 6.94-6.90 (m, 1H), 6.83 (s, 1H), 6.54-6.51 (m, 1H), 2.77 (t, J=7.2 Hz, 5H), 2.70 (t, J=7.2 Hz, 5H), 2.62 (br s, 3H), 1.99-1.90 (br s, 2H), 1.97-1.93 (m, 6H), 1.48-1.46 (m, 3H); MS (TOF): m/z (%)=428.2097 (100%) (M+H)⁺, 426.1941 (60%) (M−1)⁻.

Example—16: tert-butyl (2-((2S)-2-((E)-2-(N'-cyano-N-((1,2,3,5,6,7-hexahydro-s-indacen-4-yl)carbamoyl)sulfamidimidoyl)vinyl)-2-methylpyrrolidin-1-yl)ethyl)(methyl)carbamate

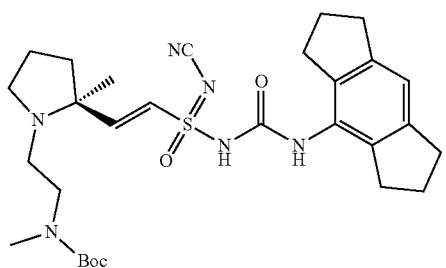 [SMILES: CN(CCN1CCC[C@@]1(C)/C=C/S(=O)(=NC#N)NC(=O)Nc1c2c(cc3c1CCC3)CCC2)C(=O)OC(C)(C)C]

¹H NMR (400 MHz, DMSO-d₆): δ=9.13 (bs, 1H), 7.84 (br s, 1H), 6.81 (s, 1H), 6.66-6.50 (m, 1H), 6.36 (d, J=15.6 Hz, 1H), 3.27-3.21 (m, 1H), 3.11-3.21 (m, 2H), 2.84-2.81 (m, 1H), 2.76 (d, J=7.2 Hz, 4H), 2.70-2.68 (m, 6H), 2.5 (s, 3H) 1.91 (quin, J=7.2 Hz, 4H), 1.75 (br s, 3H), 1.66-1.63 (m, 1H), 1.38 (s, 9H), 1.06 (s, 3H); MS (TOF): m/z (%)=571.3033 (100%) (M+H)⁺, 569.2888 (100%) (M−1)⁻.

Example—17: (E)-N'-cyano-N-((1,2,3,5,6,7-hexahydro-s-indacen-4-yl)carbamoyl)-2-((S)-1-isopropyl-2-methylpyrrolidin-2-yl)ethene-1-sulfonimidamide

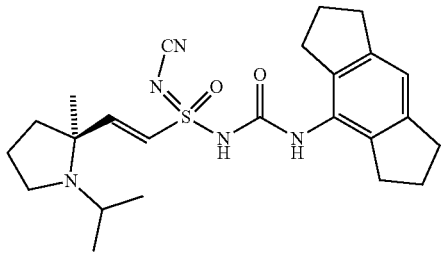 [SMILES: CC(C)N1CCC[C@@]1(C)/C=C/S(=O)(=NC#N)NC(=O)Nc1c2c(cc3c1CCC3)CCC2]

¹H NMR (400 MHz, DMSO-d₆): δ=9.41-9.10 (m, 1H), 7.97 (s, 1H), 6.94 (s, 1H), 6.86-6.80 (m, 2H), 3.63-3.55 (m, 1H), 3.45-3.41 (m, 2H), 2.77 (t, J=7.2 Hz, 4H), 2.69 (t, J=7.2 Hz, 4H), 1.95-1.88 (m, 8H), 1.49 (s, 3H), 1.26-1.22 (m, 6H); MS (TOF): m/z (%)=482.2570 (100%) (M+H)⁺.

Example—18: (E)-N'-cyano-2-((S)-1-cyclopentyl-2-methylpyrrolidin-2-yl)-N-((1,2,3,5,6,7-hexahydro-s-indacen-4-yl)carbamoyl)ethene-1-sulfonimidamide

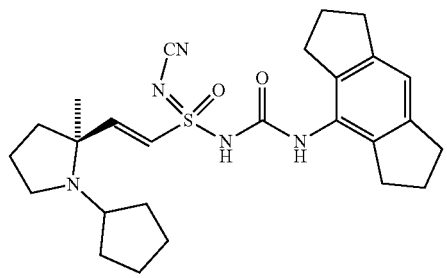 [SMILES: C[C@@]1(/C=C/S(=O)(=NC#N)NC(=O)Nc2c3c(cc4c2CCC4)CCC3)CCCN1C1CCCC1]

¹H NMR (400 MHz, DMSO-d₆) δ=9.60-9.40 (m, 1H), 7.98 (s, 1H), 7.01-6.92 (m, 1H), 6.82 (s, 1H), 6.77-6.70 (m, 1H), 3.61-3.59 (m, 1H), 3.48-3.38 (m, 2H), 2.73 (t, J=7.2 Hz, 4H), 2.63 (t, J=6.8 Hz, 4H), 2.08-2.06 (m, 1H), 1.99-1.97 (m, 3H), 1.95-1.88 (m, 6H), 1.65-1.61 (m, 4H), 1.50-1.48 (m, 5H); MS (TOF): m/z (%)=482.2570 (100%) (M+H)⁺.

Example—19: (E)-N'-cyano-2-((S)-1-cyclobutyl-2-methylpyrrolidin-2-yl)-N-((1,2,3,5,6,7-hexahydro-s-indacen-4-yl)carbamoyl)ethene-1-sulfonimidamide

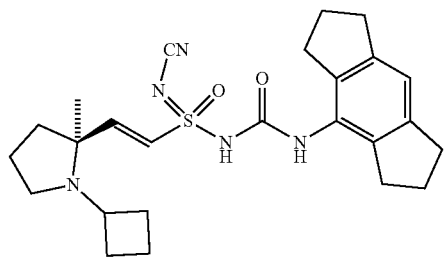 [SMILES: C[C@@]1(/C=C/S(=O)(=NC#N)NC(=O)Nc2c3c(cc4c2CCC4)CCC3)CCCN1C1CCC1]

¹H NMR (400 MHz, DMSO-d₆) δ=9.87-9.67 (m, 1H), 8.00 (s, 1H), 7.01-6.93 (m, 1H), 6.83 (s, 1H), 6.71-6.65 (m,

1H), 3.82-3.76 (m, 1H), 3.51-3.49 (m, 1H), 3.18-3.16 (m, 1H), 2.77 (t, J=7.2 Hz, 4H), 2.70-2.69 (m, 4H), 2.25-2.11 (m, 5H), 2.07-2.00 (m, 2H), 1.97-1.88 (m, 5H), 1.74-1.67 (m, 2H), 1.55-1.40(m, 3H); MS (TOF): m/z (%)=468.2407 (100%) (M+H)⁺.

Example—20: (E)-N'-cyano-N-((1,2,3,5,6,7-hexahydro-s-indacen-4-yl)carbamoyl)-2-((S)-2-methylpyrrolidin-2-yl)ethene-1-sulfonimidamide

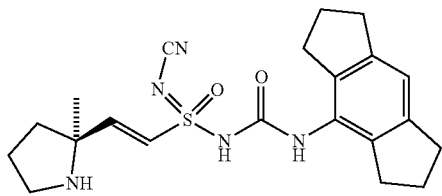 [SMILES: C[C@@]1(/C=C/S(=O)(=NC#N)NC(=O)Nc2c3c(cc4c2CCC4)CCC3)CCCN1]

¹H NMR (400 MHz, DMSO-d₆) δ=7.99 (s, 1H), 6.95 (dd, J₁=2.4 Hz, J₂=15.6 Hz, 1H), 6.82 (s, 1H), 6.63 (dd, J₁=2.0 Hz, J₂=15.6 Hz, 1H), 3.28-3.19 (m, 2H), 2.77 (t, J=7.2 Hz, 4H), 2.70 (t, J=7.2 Hz, 4H), 2.12-1.81 (m, 8H), 1.48 (s, 3H); MS (TOF): m/z (%)=417.1950 (100%) (M+H)⁺.

Example—21: (E)-N'-cyano-2-((S)-1-(cyclopropylmethyl)-2-methylpyrrolidin-2-yl)-N-((1,2,3,5,6,7-hexahydro-s-indacen-4-yl)carbamoyl)ethene-1-sulfonimidamide

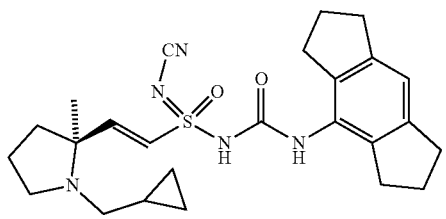 [SMILES: C[C@@]1(/C=C/S(=O)(=NC#N)NC(=O)Nc2c3c(cc4c2CCC4)CCC3)CCCN1CC1CC1]

¹-H NMR (400 MHz, DMSO-d₆) δ=9.53 (br s, 1H), 8.02 (s, 1H), 7.00-6.89 (m, 1H), 6.82 (s, 1H), 6.63-6.41 (m, 1H), 3.74 (br s, 1H), 2.97 (br s, 1H), 2.76 (t, J=7.2 Hz, 5H), 2.69 (t, J=7.2 Hz, 5H), 2.10-2.08 (m, 3H), 1.95-1.88 (m, 5H), 1.58-1.35 (m, 3H), 1.02 (br s, 1H), 0.56 (br s, 2H), 0.34-0.27(m, 2H); MS (TOF): m/z (%)=468.2419 (100%) (M+H)⁺.

Example—22: (E)-N'-cyano-N-((1,2,3,5,6,7-hexahydro-s-indacen-4-yl)carbamoyl)-2-((S)-2-methylpyrrolidin-2-yl)ethene-1-sulfonimidamide 2,2,2-trifluoroacetate

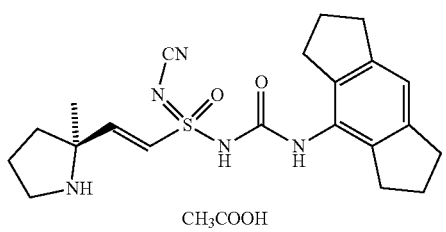

¹H NMR (400 MHz, DMSO-d₆): δ=8.98 (s, 2H), 8.02 (s, 1H), 6.97 (dd, J₁=3.2 Hz, J₂=15.2 Hz, 1H), 6.83 (s, 1H), 6.64 (dd, J₁=2.0 Hz, J₂=15.6 Hz, 1H), 3.33-3.25 (m, 2H), 2.77 (t, J=7.6 Hz, 4H), 2.70 (t, J=7.2 Hz, 4H), 2.14-1.83 (m, 8H), 1.48 (m, 3H); MS (TOF): m/z (%)=414.1925 (100%) (M+H)⁺, 412.1799 (50%) (M−1).

Example—23: (E)-N'-cyano-N-((1,2,3,5,6,7-hexahydro-s-indacen-4-yl)carbamoyl)-2-((S)-2-methyl-1-(tetrahydro-2H-pyran-4-yl)pyrrolidin-2-yl)ethene-1-sulfonimidamide

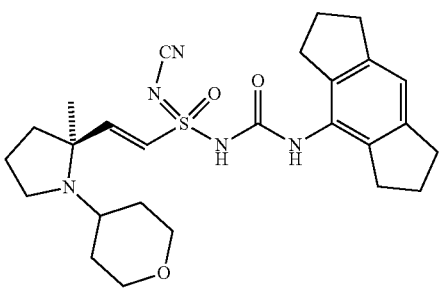 [SMILES: C[C@@]1(/C=C/S(=O)(=NC#N)NC(=O)Nc2c3c(cc4c2CCC4)CCC3)CCCN1C1CCOCC1]

¹H NMR (400 MHz, DMSO-d₆) δ=9.57 (s, 1H), 8.00 (s, 1H), 6.97-6.75 (m, 3H), 3.91-3.89 (m, 1H), 3.65 (br s, 2H), 3.44-3.39 (m, 4H), 3.27-3.18 (m, 2H), 2.76 (t, J=7.2 Hz, 4H), 2.70 (t, J=7.2 Hz, 4H), 2.09-1.97 (m, 4H), 1.92 (quin, J=7.2 Hz, 5H), 1.65-1.59 (m, 1H), 1.52 (s, 3H); MS (TOF): m/z (%)=498.2515 (100%) (M+H)⁺, 496.2353 (50%) (M−1)⁻.

Example—24: (E)-N'-cyano-N-((1,2,3,5,6,7-hexahydro-s-indacen-4-yl)carbamoyl)-2-((S)-1-isobutyl-2-methylpyrrolidin-2-yl)ethene-1-sulfonimidamide

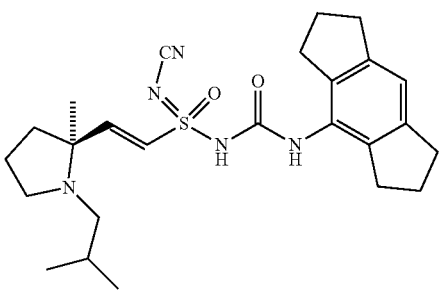 [SMILES: CC(C)CN1CCC[C@@]1(C)/C=C/S(=O)(=NC#N)NC(=O)Nc1c2c(cc3c1CCC3)CCC2]

¹H NMR (400 MHz, DMSO-d₆) δ=8.97-8.77 (m, 1H), 8.04 (s, 1H), 7.00-6.94 (m, 1H), 6.82 (s, 1H), 6.63-6.45 (m, 1H), 3.73 (br s, 1H), 3.33-3.20 (m, 2H), 2.84-2.83 (m, 1H), 2.76-2.75 (m, 4H), 2.71 (br s, 4H), 2.34-2.33 (m, 1H), 2.13-2.06 (m, 2H), 2.03-2.00 (m, 2H), 1.92 (t, J=7.2 Hz, 4H), 1.60-1.38 (m, 3H), 0.99-0.85 (s, 6H); MS (TOF): m/z (%)=470.3124 (100%) (M+H)⁺, 468.2752 (50%) (M−1)⁻;

Example—25: (E)-2-((S)-1-acetyl-2-methylpyrrolidin-2-yl)-N'-cyano-N-((1,2,3,5,6,7-hexahydro-s-indacen-4-yl)carbamoyl)ethene-1-sulfonimidamide

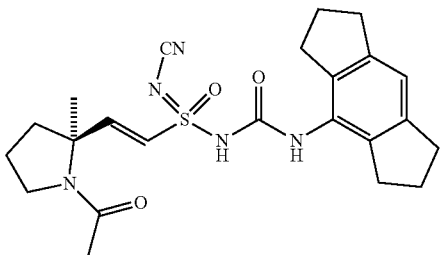 [SMILES: CC(=O)N1CCC[C@@]1(C)/C=C/S(=O)(=NC#N)NC(=O)Nc1c2c(cc3c1CCC3)CCC2]

$^1$H NMR (400 MHz, DMSO-d$_6$) δ=7.84 (s, 1H), 7.08 (s, 1H), 6.81 (s, 1H), 6.61 (d, J=15.2 Hz, 1H), 6.51-6.46 (m, 1H), 3.52-3.40(m, 2H), 2.77 (t, J=7.2 Hz, 4H), 2.70 (t, J=7.2 Hz, 4H), 2.01-1.88 (m, 8H), 1.79-1.76 (m, 3H), 1.51-1.50 (m, 3H); MS (TOF): m/z (%)=456.2050 (100%) (M+H)$^+$, 454.1904 (50%) (M−1)$^−$.

Example—26: (E)-N'-cyano-2-((S)-1-ethyl-2-methylpyrrolidin-2-yl)-N-((1,2,3,5,6,7-hexahydro-s-indacen-4-yl)carbamoyl)ethene-1-sulfonimidamide

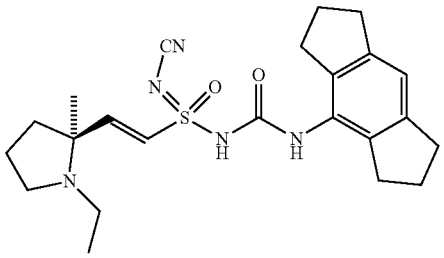 [SMILES: CCN1CCC[C@@]1(C)/C=C/S(=O)(=NC#N)NC(=O)Nc1c2c(cc3c1CCC3)CCC2]

$^1$H NMR (400 MHz, DMSO-d$_6$) δ=9.54 (s, 1H), 8.03 (s, 1H), 6.98 (d, J=15.6 Hz, 1H), 6.83 (s, 1H), 6.60-6.54 (m, 1H), 3.65 (br s, 1H), 3.34-3.10 (m, 2H), 2.92 (br s, 1H), 2.77 (t, J=7.2 Hz, 4H), 2.70 (t, J=6.8 Hz, 4H), 2.10-2.08 (m, 4H), 1.96-1.88 (m, 4H), 1.57-1.37 (m, 3H), 1.18 (br s, 3H); MS (TOF): m/z (%)=442.2255 (100%) (M+H)$^+$, 440.2115 (50%) (M−1)$^−$

Example—27: (E)-N'-cyano-2-((S)-1-cyclohexyl-2-methylpyrrolidin-2-yl)-N-((1,2,3,5,6,7-hexahydro-s-indacen-4-yl)carbamoyl)ethene-1-sulfonimidamide

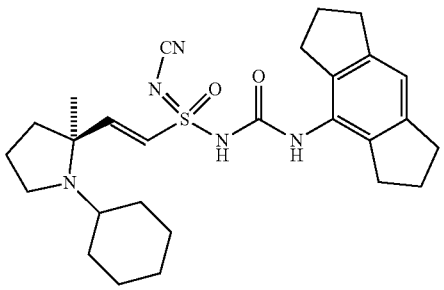 [SMILES: C[C@@]1(/C=C/S(=O)(=NC#N)NC(=O)Nc2c3c(cc4c2CCC4)CCC3)CCCN1C1CCCCC1]

$^1$H NMR (400 MHz, DMSO-d$_6$) δ=9.37 (s, 1H), 8.03 (s, 1H), 6.94-6.82 (m, 3H), 3.65-3.64 (m, 1H), 3.28-3.16 (m, 1H), 2.76 (t, J=7.2 Hz, 4H), 2.70 (t, J=7.2 Hz, 4H), 2.10-2.07 (m, 1H), 1.99-1.88 (m, 8H), 1.76-1.72 (m, 1H), 1.63 (br s, 2H), 1.49 (br s, 3H), 1.34-1.14 (m, 5H), 1.05-1.02 (m, 1H); MS (TOF): m/z (%)=496.2716 (100%) (M+H)$^+$, 494.2576 (50%) (M−1)$^−$.

Example—28: (E)-N'-cyano-N-((1,2,3,5,6,7-hexahydro-s-indacen-4-yl)carbamoyl)-2-((S)-1-(2-methoxyethyl)-2-methylpyrrolidin-2-yl)ethene-1-sulfonimidamide

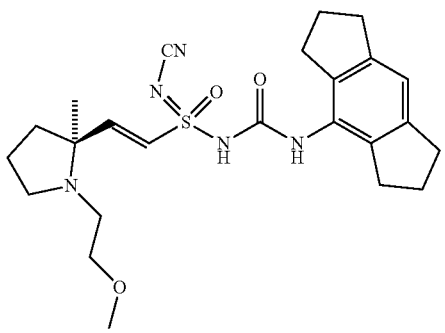 [SMILES: COCCN1CCC[C@@]1(C)/C=C/S(=O)(=NC#N)NC(=O)Nc1c2c(cc3c1CCC3)CCC2]

$^1$H NMR (400 MHz, DMSO-d$_6$): δ=6.91 (s, 1H), 6.84-6.75 (m, 1H), 6.54 (d, J=15.2 Hz, 1H), 6.39 (d, J=15.6 Hz, 1H), 3.28 (t, J=6.4 Hz, 2H), 3.06-3.05 (m, 2H), 2.81-2.78 (m, 4H), 2.76-2.61 (m, 4H), 1.98-1.99 (m, 4H), 1.91-1.86 (m, 7H), 1.76-1.69 (m, 2H), 1.34 (s, 3H); MS (TOF): m/z (%)=472.2357 (100%) (M+H)$^+$, 440.2115 (50%) (M−1)$^−$.

Example—29: (E)-N'-cyano-N-((1,2,3,5,6,7-hexahydro-s-indacen-4-yl)carbamoyl)-2-((S)-2-methyl-1-(thiazol-2-ylmethyl)pyrrolidin-2-yl)ethene-1-sulfonimidamide

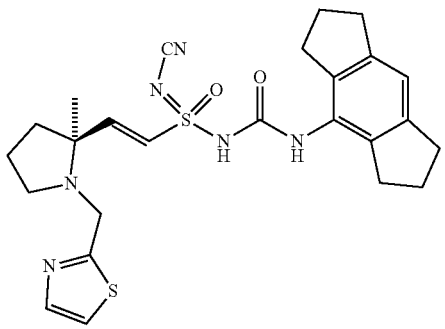 [SMILES: C[C@@]1(/C=C/S(=O)(=NC#N)NC(=O)Nc2c3c(cc4c2CCC4)CCC3)CCCN1Cc1nccs1]

$^1$H NMR (400 MHz, DMSO-d$_6$): δ=7.87 (s, 1H), 7.70-7.63 (m, 2H), 6.80 (s, 1H), 6.69 (br s, 1H), 6.50 (d, J=14.8 Hz, 1H), 3.87-3.86 (m, 2H), 2.81-2.73 (m, 5H), 2.70-2.60 (m, 5H), 1.95-1.84 (m, 8H), 1.23 (b s, 3H); MS (TOF): m/z (%)=511.1927 (100%) (M+H)$^+$, 509.1764 (50%) (M−1)$^−$.

Example—30: (E)-N'-cyano-N-((1,2,3,5,6,7-hexa-hydro-s-indacen-4-yl)carbamoyl)-2-((S)-2-methyl-1-(2-methyl-2-(pyrrolidin-1-yl)propyl)pyrrolidin-2-yl)ethene-1-sulfonimidamide

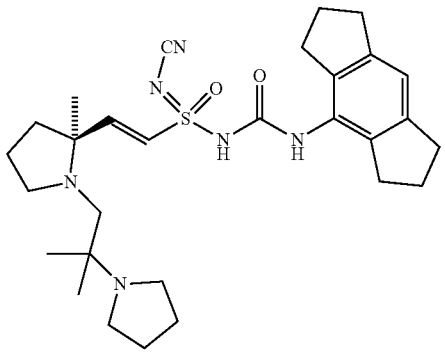 [SMILES: CC(C)(CN1CCC[C@@]1(C)/C=C/S(=O)(=NC#N)NC(=O)Nc1c2c(cc3c1CCC3)CCC2)N1CCCC1]

$^1$H NMR (400 MHz, DMSO-d$_6$) δ=8.81 (br s, 1H), 8.17 (s, 1H), 6.85 (s, 1H), 6.51 (d, J=15.2 Hz, 1H), 6.35 (d, J=15.6 Hz, 1H), 3.16-3.06 (m, 4H), 2.77 (d, J=15.6 Hz, 5H), 2.70-2.66 (m, 7H), 2.02-1.86 (m, 6H), 1.79-1.53 (m, 6H), 1.22 (s, 3H), 1.06 (d, J=2.8 Hz, 6H); MS (TOF): m/z (%)=539.3143 (100%) (M+H)$^+$, 537.2990 (50%) (M−1)$^−$.

Example—31: (2S)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxamide

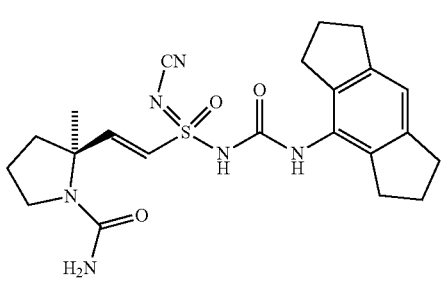 [SMILES: C[C@@]1(/C=C/S(=O)(=NC#N)NC(=O)Nc2c3c(cc4c2CCC4)CCC3)CCCN1C(N)=O]

$^1$H NMR (400 MHz, DMSO-d$_6$) δ=7.86 (s, 1H), 6.81 (s, 1H), 6.61 (dd, J$_1$=5.6, J$_2$=15.2 Hz, 1H), 6.46 (dd, J$_1$=8.0 Hz, J$_2$=15.2, 1H), 5.57 (d, J=4.4 Hz, 2H), 3.31 (br s, 2H), 2.76 (t, J=7.2 Hz, 4H), 2.69 (t, J=7.2 Hz, 4H), 1.95-1.90 (m, 5H), 1.88 (br s, 3H), 1.48-1.47 (m, 3H);

Example—32: sodium ((E)-N-cyano-2((S)-1-isobutyl-2-methylpyrrolidin-2-yl)vinylsulfonimidoyl)((1,2,3,5,6,7-hexahydro-s-indacen-4-yl)carbamoyl)amide $^1$H NMR (400 MHz, DMSO-d$_6$): δ=7.83 (s, 1H), 6.81 (s, 1H), 6.61 (d, J=15.6 Hz, 1H), 6.38 (dd, J$_1$=1.6 Hz, J$_2$=15.6, 1H), 2.76 (t, J=7.2 Hz, 5H), 2.68 (t, J=7.2 Hz, 4H), 2.65-2.61 (m, 1H), 2.11-2.08 (m, 2H), 1.91 (t, J=7.2 Hz, 4H), 1.75-1.72 (m, 3H), 1.66-1.56 (m, 2H), 1.05 (d, J=3.2 Hz, 3H), 0.85-0.80 (m, 6H); MS (TOF): m/z (%)=470.2568 (100%) (M−Na+H)$^+$.

Example—33: sodium ((E)-N-cyano-2-((S)-1-cyclohexyl-2-methylpyrrolidin-2-yl)vinylsulfonimidoyl)((1,2,3,5,6,7-hexahydro-s-indacen-4-yl)carbamoyl)amide

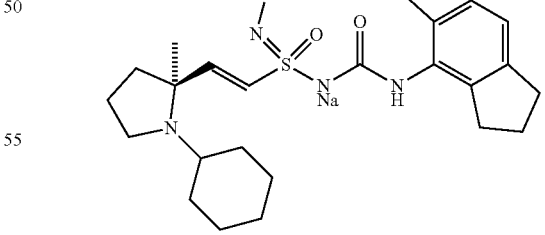

$^1$H NMR (400 MHz, DMSO-d$_6$) δ=7.81 (s, 1H), 6.81 (s, 1H), 6.60 (dd, J$_1$=3.2, J$_2$=15.6 Hz, 1H), 6.46 (d, J=15.6, 1H), 2.92-2.89 (m, 1H), 2.76 (t, J=7.2 Hz, 4H), 2.69 (t, J=7.2 Hz, 4H), 2.40-2.30 (m, 1H), 1.95-1.88 (m, 4H), 1.76-1.66 (m, 6H), 1.61-1.56 (m, 3H), 1.52-1.48 (m, 1H), 1.26-1.13 (m, 4H), 1.04 (s, 3H), 1.01-0.98 (m, 1H); MS (TOF): m/z (%)=496.2710 (100%) (M−Na+H)$^+$.

Example—34: tert-butyl (2R)-2-((E)-2-(N'-cyano-N-((1,2,3,5,6,7-hexahydro-s-indacen-4-yl)carbamoyl)sulfamidimidoyl)vinyl)pyrrolidine-1-carboxylate

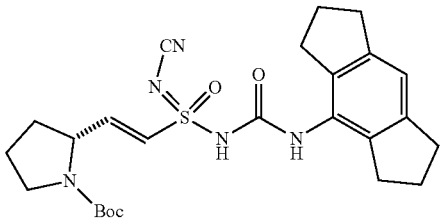

$^1$H NMR (400 MHz, DMSO-$d_6$): δ=7.80 (s, 1H), 6.80 (s, 1H), 6.54-6.46 (m, 1H), 6.33-6.28 (m, 1H), 4.32-4.30 (m, 1H), 3.28-3.25(m, 2H), 2.77 (t, J=7.2 Hz, 4H), 2.72 (t, J=7.2 Hz, 4H), 1.91 (quin, J=7.2 Hz, 4H), 1.79-1.70 (m, 4H), 1.40 (s, 9H); MS (TOF): m/z (%)=500.2700 (100%) (M+H)$^+$.

Example—35: (E)-N-((1,2,3,5,6,7-hexahydro-s-indacen-4-yl)carbamoyl)-N'-methyl-2-((R)-pyrrolidin-2-yl)ethene-1-sulfonimidamide 2,2,2-trifluoroacetate

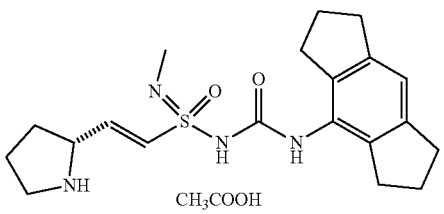

$^1$H NMR (400 MHz, DMSO-$d_6$): δ=9.3 (br s, 1H), 8.98 (br s, 1H), 8.45 (s, 1H), 6.89 (s, 1H), 6.85-6.84 (m, 1H), 6.72-6.67 (m, 1H), 4.33 (br s, 1H), 3.29-3.25 (m, 2H), 2.79 (t, J=7.2 Hz, 4H), 2.71 (t, J=6.8 Hz, 4H), 2.55-2.51 (m, 3H), 2.21-2.19 (m, 1H), 2.02-1.93 (m, 6H), 1.82-1.74 (m, 1H); MS (ESI): m/z (%)=389.4 (90%) (M+H)$^+$.

Example—36: (E)-2-((S)-1,2-dimethylpyrrolidin-2-yl)-N-((1,2,3,5,6,7-hexahydro-s-indacen-4-yl)carbamoyl)-N'-methylethene-1-sulfonimidamide

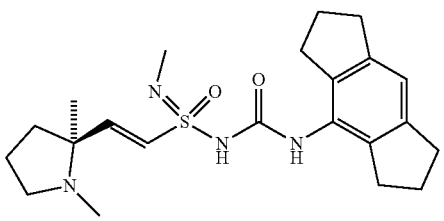 [SMILES: CN=S(=O)(/C=C/[C@]1(C)CCCN1C)NC(=O)Nc1c2c(cc3c1CCC3)CCC2]

$^1$H NMR (400 MHz, DMSO-$d_6$) δ=8.40 (br s, 1H), 7.00 (s, 1H), 6.88 (s, 1H), 6.56 (d, J=15.2 Hz, 1H), 6.45 (dd, $J_1$=6.4 Hz, $J_2$=15.6 Hz, 1H), 2.79 (t, J=7.2 Hz, 5H), 2.70 (t, J=6.8 Hz, 6H), 2.14 (s, 3H), 1.94 (quin, J=7.2 Hz, 6H), 1.77-1.72 (m, 4H), 1.24-1.10 (m, 3H); MS (TOF): m/z (%)=417.2207 (100%) (M+H)$^+$.

Biological Activity:
In-Vitro Assays:

THP1 monocytes were differentiated with PMA (100 ng/mL) and incubated at 37° C. for 20 hours in presence of 5% $CO_2$. 2×10$^5$ differentiated cells were plated per well of 96 well tissue culture plates. The cells were primed using 500 ng/mL Lipopolysaccharide and incubating for 4 hrs under the same condition. The cells were then treated with various concentrations of the compounds for 30 min followed by treatment with 5 mM ATP for 1 hr. The supernatants were collected and analysed by IL-1b (Mabtech Cat #3415-1H-20) or TNF-a (Mabtech; Cat #3510-1H-20) detection kit. The data were analyzed using GraphPad Prism V7.0. Dose Response Curve (DRC) was constructed to determine the $IC_{50}$ value by fitting percentage cell survival data to the GraphPad Prism using nonlinear regression analysis. The invitro IL-1β inhibitory activity ($IC_{50}$) for representative compounds are listed in Table 1.

TABLE 1

| Compound | $IC_{50}$ (μM) |
|---|---|
| Example 3 | 19 |
| Example 4 | 20 |
| Example 7 | 1.5 |
| Example 8 | 12 |
| Example 9 | 11 |
| Example 10 | 6.4 |
| Example 11 | 2.3 |
| Example 13 | 4 |
| Example 14 | 9 |
| Example 15 | 2.1 |
| Example 17 | 11 |
| Example 18 | 18 |
| Example 19 | 4.6 |
| Example 20 | 3.2 |
| Example 21 | 4.6 |
| Example 22 | 8.9 |
| Example 24 | 15 |
| Example 25 | 19 |
| Example 26 | 19 |
| Example 29 | 15 |
| Example 31 | 9.2 |
| Example 34 | 19 |

In-Vivo Efficacy Studies:

Demonstration of in vivo efficacy of test compounds in rats mice, oral routes of administration.

Animals

All the animal experiments were carried out in female rats and mice, bred in-house. Animals were housed in groups of 6 animals per cage, for a week, in order to habituate them to vivarium conditions (25±4° C., 60-65% relative humidity, 12: 12 h light: dark cycle, with lights on at 7.30 am). All the animal experiments were carried out according to the internationally valid guidelines following approval by the 'Zydus Research Center animal ethical committee'.

In-Vivo LPS and ATP Induced IL-1β Assay:

Female C57 mice (6-8 weeks) received intraperitoneal injection of 50 μg/mouse of lipopolysaccharide (LPS) in PBS. Animals were treated immediately with the test compounds or the vehicle. After 2 h of LPS injection, animals were administered with ATP at 12.5 mg/mouse dissolved in PBS via intraperitoneal route. After 30 minutes of ATP injection, serum was collected for IL-1β estimation by ELISA.

The novel compounds of the present invention can be formulated into suitable pharmaceutically acceptable compositions by combining with suitable excipients by techniques and processes and concentrations as are well known.

The compounds of formula (I) or pharmaceutical compositions containing them are useful as a medicament for the inhibition of NLRP3 activity and suitable for humans and other warm blooded animals, and may be administered either by oral, topical or parenteral administration.

Thus, a pharmaceutical composition comprising the compounds of the present invention may comprise a suitable binder, suitable bulking agent &/or diluent and any other suitable agents as may be necessary. Optionally, the pharmaceutical composition may be suitably coated with suitable coating agents.

The compounds of the present invention, Formula (I) are NLRP3 inhibitors and are useful in the treatment of disease states mediated by NLRP3, preferably diseases or conditions in which interleukin 1β activity is implicated and related disorders, including inflammation, gouty arthritis, Inflammatory bowel disease (IBD), type 2 diabetes, atherosclerosis, and liver fibrosis. More particularly, embodiments of the present invention are useful as therapeutics in the treatment of a variety of pathological conditions including (but not limited to) lymphoma, auto-immune diseases, heteroimmune diseases, inflammatory diseases, type 1 diabetes, chronic inflammation, cancer, and neurodegenerative diseases or conditions.

The quantity of active component, that is, the compounds of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The compounds of the present invention, formula (I), may be used alone or in any combination with one or more other therapeutic agents which a skilled medical practitioner can easily identify. Such other therapeutic agent may be selected depending on the type of disease being treated, the severity, other medications being taken by the patients etc. Thus for example, for treatment of rheumatoid arthritis, one or more DMARDs may be used in combination with the compounds of the present invention.

In one of the embodiments compound of formula (I) of the present invention may be used in combination with one or more suitable pharmaceutically active agents selected from following therapeutic agents in any combination such as inhibitors of interleukin-1β (e.g. rilonacept, canakinumab, and anakinra); immune-suppressants (e.g., Methotrexate, mercaptopurine, cyclophosphamide), Mesalamine, Cyclosporine, metabolic disorders drugs, glucocorticoids, non-steroidal anti-inflammatory drugs, Cox-2 specific inhibitors, TNF-a binding proteins (eg., Infliximab, etanercept), interferon-13, interferon, interleukin-2, antihistamines, beta-agonist, BTK inhibitors, anticolinergics, anti-cancer agents or their suitable pharmaceutically acceptable salts. Further examples for use in combination with Non-Alcoholic Steato-Hepatitis (NASH) and fibrosis drugs, anti-cancer antibiotics, hormones, Aromatase inhibitors, antibodies, cytokines, vaccines, drug conjugates, inhibitors of mitogen-activated protein kinase signaling (ex: BAY 43-9006), Syk inhibitors, mTOR inhibitors, antibodies (Rituxan), and BCR/ABL antagonist.

Compositions of the invention are also used in combination with other active ingredients. For the treatment of Arenaviridae virus infections, preferably, the other active therapeutic agent is active against Arenaviridae virus infections, particularly Lassa virus and Junin virus infections. Non-limiting examples of these other active therapeutic agents are Ribavirin, Favipiravir (also known as T-705 or Avigan), T-705 monophosphate, T-705 diphosphate, T-705 triphosphate, ST-193, and mixtures thereof. The compounds and compositions of the present invention are also intended for use with general care provided patients with Arenaviridae viral infections, including parenteral fluids (including dextrose saline and Ringer's lactate) and nutrition, antibiotic (including Metronidazole and Cephalosporin antibiotics, such as Ceftriaxone and Cefuroxime) and/or antifungal prophylaxis, fever and pain medication, antiemetic (such as Metoclopramide) and/or antidiarrheal agents, vitamin and mineral supplements (including Vitamin C or/and K and zinc sulfate), anti-inflammatory agents (such as Ibuprofen), pain medications, and medications for other common diseases in the patient population, such anti-malarial agents (including Artemether and Artesunate-lumefantrine combination therapy), typhoid (including quinolone antibiotics, such as Ciprofloxacin, macrolide antibiotics, such as Azithromycin, cephalosporin antibiotics, such as Ceftriaxone, or aminopenicillins, such as Ampicillin), or shigellosis.

While the present invention has been described in terms of its specific embodiments, certain modifications and equivalents will be apparent to those skilled in the art and are intended to be included within the scope of the present invention.

We claim:

1. Compound(s) having structure of general formula (I)

Formula (I)

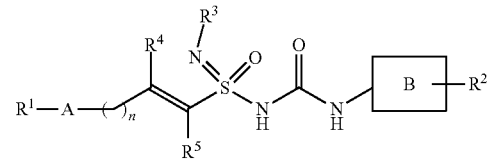

their tautomeric forms, their stereoisomers, their enantiomers, their pharmaceutically acceptable salts, and pharmaceutical compositions containing them wherein, 'A' is selected from optionally substituted groups selected from $(C_3-C_8)$ cycloalkyl, $(C_6-C_{10})$aryl, heteroaryl, and heterocyclyl groups each of which is optionally further substituted with one or more than one heteroatom(s);

B' is the following ring system

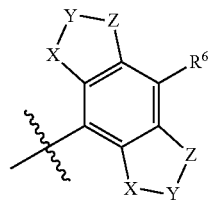

$R^1$ at each occurrence is independently selected from hydrogen, halogen, haloalkyl, optionally substituted groups selected from $(C_1-C_6)$alkyl, $(C_1-C_6)$alkoxy, $(C_3-C_6)$cycloalkyl, $(C_6-C_{10})$aryl, heterocyclyl, thiol, $(C_1-C_6)$ mercapto alkyl, $SO_2(C_6-C_{10})$aryl, $SO_2(C_3-C_6)$cycloalkyl, $C_1-C_6$(thio-alkoxy), $CO(O)(C_1-C_6)$alkyl;

R² is hydrogen;

n is 0;

R³ at each occurrence is independently selected from hydrogen, cyano, optionally substituted groups selected from (C₁-C₁₀)alkyl;

R⁴ and R⁵ are independently hydrogen.

2. The compound(s) as claimed in claim 1, wherein when any of above defined group is substituted, the substitutions on them may be selected from those described above or may additionally be selected from hydrogen, hydroxy, cyano, halo, haloalkyl, haloalkyloxy, alkylthio (C₁-C₆)alkyl, (C₂-C₆)alkenyl, (C₂-C₆)alkynyl, (C₃-C₇)cycloalkyl, (C₁-C₆) alkoxy, —COR₁₂, —CSR₁₂, C(O)OR₁₂, C(O)—R¹², —C(O)—NR₁₂R₁₃, —C(S)—NR₁₂R₁₃, —SO₂R₁₂ group, wherein each of R₁₂ and R₁₃ is independently selected from hydrogen, optionally substituted group selected from (C₁-C₆)alkyl, (C₂-C₆)alkenyl, (C₂-C₆)alkynyl, (C₃-C₇)cycloalkyl, aryl, heteroaryl, heterocyclyl groups.

3. The compound as claimed in claim 1 is selected from the group comprising;

tert-butyl (2R)-2-((E)-2-(N-((1,2,3,5,6,7-hexahydro-s-indacen-4-yl)carbamoyl)sulfamidimidoyl)vinyl)pyrrolidine-1-carboxylate;

tert-butyl (2S)-2-((E)-2-(N-((1,2,3,5,6,7-hexahydro-s-indacen-4-yl)carbamoyl)sulfamidimidoyl)vinyl)-2-methylpyrrolidine-1-carboxylate;

tert-butyl (2S)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxylate;

(E)-N'-cyano-N-((1,2,3,5,6,7-hexahydro-s-indacen-4-yl)carbamoyl)-2-((S)-2-methylpyrrolidin-2-yl)ethene-1-sulfonimidamide hydrochloride;

(E)-2-((S)-1,2-dimethylpyrrolidin-2-yl)-N-((1,2,3,5,6,7-hexahydro-s-indacen-4-yl)carbamoyl)ethene-1-sulfonimidamide;

(E)-2-((S)-1,2-dimethylpyrrolidin-2-yl)-N-((1,2,3,5,6,7-hexahydro-s-indacen-4-yl)carbamoyl)-N'-methylethene-1-sulfonimidamide;

(E)-N'-cyano-2-((S)-1,2-dimethylpyrrolidin-2-yl)-N-((1,2,3,5,6,7-hexahydro-s-indacen-4-yl)carbamoyl)ethene-1-sulfonimidamide;

(E)-N'-cyano-2-((R)-1-(cyclohexylsulfonyl) pyrrolidin-2-yl)-N-((1,2,3,5,6,7-hexahydro-s-indacen-4-yl)carbamoyl)ethene-1-sulfonimidamide;

(E)-N'-cyano-2-((R)-1-((2-cyanophenyl) sulfonyl) pyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((R)-pyrrolidin-2-yl)ethene-1-sulfonimidamide hydrochloride;

(E)-N'-cyano-N-((1,2,3,5,6,7-hexahydro-s-indacen-4-yl)carbamoyl)-2-((R)-1-methylpyrrolidin-2-yl)ethene-1-sulfonimidamide;

tert-butyl (2R)-2-((E)-2-(N-((1,2,3,5,6,7-hexahydro-s-indacen-4-yl)carbamoyl)sulfamidimidoyl)vinyl)-2-methylpyrrolidine-1-carboxylate;

tert-butyl (2R)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxylate;

(E)-N'-cyano-N-((1,2,3,5,6,7-hexahydro-s-indacen-4-yl)carbamoyl)-2-((R)-2-methylpyrrolidin-2-yl)ethene-1-sulfonimidamide hydrochloride;

(E)-N'-cyano-2-((R)-1,2-dimethylpyrrolidin-2-yl)-N-((1,2,3,5,6,7-hexahydro-s-indacen-4-yl)carbamoyl)ethene-1-sulfonimidamide;

tert-butyl (2-((2S)-2-((E)-2-(N'-cyano-N-((1,2,3,5,6,7-hexahydro-s-indacen-4-yl)carbamoyl)sulfamidimidoyl)vinyl)-2-methylpyrrolidin-1-yl)ethyl)(methyl) carbamate;

(E)-N'-cyano-N-((1,2,3,5,6,7-hexahydro-s-indacen-4-yl)carbamoyl)-2-((S)-1-isopropyl-2-methylpyrrolidin-2-yl)ethene-1-sulfonimidamide;

(E)-N'-cyano-2-((S)-1-cyclopentyl-2-methylpyrrolidin-2-yl)-N-((1,2,3,5,6,7-hexahydro-s-indacen-4-yl)carbamoyl)ethene-1-sulfonimidamide;

(E)-N'-cyano-2-((S)-1-cyclobutyl-2-methylpyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((S)-2-methylpyrrolidin-2-yl)ethene-1-sulfonimidamide;

(E)-N'-cyano-2-((S)-1-(cyclopropylmethyl)-2-methylpyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((S)-2-methylpyrrolidin-2-yl)ethene-1-sulfonimidamide 2,2,2-trifluoroacetate;

(E)-N'-cyano-N-((1,2,3,5,6,7-hexahydro-s-indacen-4-yl)carbamoyl)-2-((S)-2-methyl-1-(tetrahydro-2H-pyran-4-yl) pyrrolidin-2-yl)ethene-1-sulfonimidamide;

(E)-N'-cyano-N-((1,2,3,5,6,7-hexahydro-s-indacen-4-yl)carbamoyl)-2-((S)-1-isobutyl-2-methylpyrrolidin-2-yl) ethene-1-sulfonimidamide;

(E)-2-((S)-1-acetyl-2-methylpyrrolidin-2-yl)-N'-cyano-N-((1,2,3,5,6,7-hexahydro-s-indacen-4-yl)carbamoyl) ethene-1-sulfonimidamide;

(E)-N'-cyano-2-((S)-1-ethyl-2-methylpyrrolidin-2-yl)-N-((1,2,3,5,6,7-hexahydro-s-indacen-4-yl)carbamoyl) ethene-1-sulfonimidamide;

(E)-N'-cyano-2-((S)-1-cyclohexyl-2-methylpyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((S)-1-(2-methoxyethyl)-2-methylpyrrolidin-2-yl)ethene-1-sulfonimidamide;

(E)-N'-cyano-N-((1,2,3,5,6,7-hexahydro-s-indacen-4-yl)carbamoyl)-2-((S)-2-methyl-1-(thiazol-2-ylmethyl) pyrrolidin-2-yl)ethene-1-sulfonimidamide;

(E)-N'-cyano-N-((1,2,3,5,6,7-hexahydro-s-indacen-4-yl)carbamoyl)-2-((S)-2-methyl-1-(2-methyl-2-(pyrrolidin-1-yl)propyl)pyrrolidin-2-yl)ethene-1-sulfonimidamide;

(2S)-2-((E)-2-(N'-cyano-N-((1,2,3,5,6,7-hexahydro-s-indacen-4-yl)carbamoyl)sulfamidimidoyl)vinyl)-2-methylpyrrolidine-1-carboxamide;

sodium ((E)-N-cyano-2-((S)-1-isobutyl-2-methylpyrrolidin-2-yl)vinylsulfonimidoyl)((1,2,3,5,6,7-hexahydro-s-indacen-4-yl)carbamoyl)amide;

sodium ((E)-N-cyano-2-((S)-1-cyclohexyl-2-methylpyrrolidin-2-yl) vinylsulfonimidoyl)((1,2,3,5,6,7-hexahydro-s-indacen-4-yl)carbamoyl)amide;

tert-butyl (2R)-2-((E)-2-(N'-cyano-N-((1,2,3,5,6,7-hexahydro-s-indacen-4-yl)carbamoyl)sulfamidimidoyl)vinyl)pyrrolidine-1-carboxylate;

(E)-N-((1,2,3,5,6,7-hexahydro-s-indacen-4-yl)carbamoyl)-N'-methyl-2-((R)-pyrrolidin-2-yl)ethene-1-sulfonimidamide 2,2,2-trifluoroacetate;

(E)-2-((S)-1,2-dimethylpyrrolidin-2-yl)-N-((1,2,3,5,6,7-hexahydro-s-indacen-4-yl)carbamoyl)-N'-methylethene-1-sulfonimidamide.

4. A pharmaceutical composition comprising a therapeutically effective amount of a compound of Formula (I) as claimed in claim 1 and optionally one or more pharmaceutically acceptable carriers, diluents or excipients.

5. A method of treating diseases medicated by the NLRP3 modulators as well as treatment of diseases or conditions in which interleukin 1β activity and interleukin-18 (IL-18) are implicated, which comprise the step of administering to a patient in need thereof an effective amount of a compound of Formula (I) as claimed in claim 1 or its suitable pharmaceutical composition.

6. A method of treating a disease medicated by an NLRP3 modulator comprising the step of administering to a patient in need thereof an effective amount of a compound of Formula (I) as claimed in claim 1, wherein the NLRP3 modulator has a pathophysiological function.

7. A method of treating a disease medicated by an NLRP3 modulator comprising the step of administering to a patient in need thereof an effective amount of a pharmaceutical composition as claimed in claim 4, wherein the NLRP3 modulator has a pathophysiological function.

* * * * *